US006805244B1

(12) United States Patent
Toelken

(10) Patent No.: US 6,805,244 B1
(45) Date of Patent: Oct. 19, 2004

(54) ULTRASOUND QUALITY INSPECTION OF AVIAN EGGS

(75) Inventor: L. Taizo Toelken, Neosho, MO (US)

(73) Assignee: Ultra Hatch, Inc., Neosho, MO (US)

(*) Notice: Subject to any disclaimer, the term of this patent is extended or adjusted under 35 U.S.C. 154(b) by 131 days.

(21) Appl. No.: 10/196,803

(22) Filed: Jul. 16, 2002

Related U.S. Application Data

(63) Continuation-in-part of application No. 10/076,035, filed on Feb. 14, 2002.
(60) Provisional application No. 60/269,281, filed on Feb. 16, 2001.

(51) Int. Cl.[7] .............................................. A01K 43/04
(52) U.S. Cl. ........................ 209/510; 209/511; 119/6.8; 73/579
(58) Field of Search ................................ 209/510, 511; 119/6.8; 73/579, 587, 627–630

(56) References Cited

U.S. PATENT DOCUMENTS

| 3,503,501 A | 3/1970 | Seaborn ...................... 209/510 |
| 3,511,367 A | 5/1970 | Bliss .......................... 209/510 |
| 3,550,586 A | 12/1970 | Balamuth ...................... 601/2 |
| 3,744,299 A | 7/1973 | Bliss ........................... 73/595 |
| 3,941,122 A | 3/1976 | Jones ....................... 128/24 A |

(List continued on next page.)

FOREIGN PATENT DOCUMENTS

| DE | 3904675 | 8/1990 |
| JP | 62-151749 | 7/1987 |

OTHER PUBLICATIONS

Embrex, Inc., Press Release, entitled "Embrex Awarded U.S. Patent for its Poultry Gender Sort Technology," (Business Wire: Mar. 8, 2001).

Bill Spindle, "Masters of a Dying Art in Japan get together Yearly to Sex Chicks," (Wall Street Journal: Feb. 7, 2001), p. A1, continuing over onto p. A12.

Dr. Marianne Chat, "Burn Care: Eliminating the Waiting Game," of University of California at Irvine's serial *Milestones in Medicine,* (copyrighted 2001).

Brochure of SecondWave Systems, Inc., entitled "Non-contact Ultrasound," (copyrighted 1999).

Operating Manual of Ultramark A4 System, sheets 4–1 through 4–3 of Chapter 4 entitled "System Control Descriptions," not dated.

Selections from S.E. Solomon, *Egg & Eggshell Quality* (Iowa State Univ. 1997):—Chap. 5 "Surface defects?," Chap. 6 "Physiochemical changes in oviducal architecture," & Chap. 9 "Reinterpretation of eggshell strength."

*Primary Examiner*—Donald P. Walsh
*Assistant Examiner*—Matthew J. Kohner
(74) *Attorney, Agent, or Firm*—Jonathan A. Bay

(57) ABSTRACT

A method for making a quality determination in avian eggs, such as relating to fertility or hatching or hatchling viability, comprises the following activities. A process line is equipped to process an endless succession of eggs at an early opportunity. The process line has an ultrasound inspection station for the eggs. The ultrasound inspection results are analyzed to make a finding correlatable to the egg's shell quality, which in turn is correlatable to such quality factors as fertility or hatching or hatchling viability. A sorting determination is made based on this analysis as to which output category the egg should be sorted. The output categories might number three or so including qualified premium as for graduation to hatchery operation, not qualified for hatchery but not waste, and flunked because unusable and hence waste. The intermediate category might include graded for pet consumption.

15 Claims, 25 Drawing Sheets

U.S. PATENT DOCUMENTS

| | | | |
|---|---|---|---|
| 3,994,292 A | 11/1976 | Goodwin | 128/172 |
| 4,161,366 A * | 7/1979 | Bol et al. | 356/56 |
| 4,191,130 A | 3/1980 | Musgrave | 119/22 |
| 4,311,044 A | 1/1982 | Marshall et al. | 73/146 |
| 4,417,663 A | 11/1983 | Suzuki | 209/587 |
| 4,681,565 A | 7/1987 | Gourlandt | 604/115 |
| 4,895,157 A | 1/1990 | Nambu | 128/653 |
| 4,919,798 A * | 4/1990 | von Asselt et al. | 209/510 |
| 5,017,003 A | 5/1991 | Keromnes et al. | 356/53 |
| 5,062,296 A | 11/1991 | Migliori | 73/579 |
| 5,131,274 A | 7/1992 | Schouenborg | 73/595 |
| 5,170,698 A | 12/1992 | Kirk | 99/472 |
| 5,195,925 A | 3/1993 | Gorans | 452/166 |
| 5,199,380 A | 4/1993 | Keromnes et al. | 119/22 |
| 5,277,320 A | 1/1994 | Corkill et al. | 209/511 |
| 5,371,483 A | 12/1994 | Bhardwaj | 333/149 |
| 5,402,786 A | 4/1995 | Drummond | 128/653.2 |
| 5,426,977 A | 6/1995 | Johnston et al. | 73/595 |
| 5,485,751 A | 1/1996 | Karbach et al. | 73/618 |
| 5,589,211 A * | 12/1996 | Cox et al. | 426/298 |
| 5,617,782 A | 4/1997 | Thomas | 99/500 |
| 5,651,731 A | 7/1997 | Gorans et al. | 606/164 |
| 5,679,514 A | 10/1997 | Baker | 435/6 |
| 5,696,325 A | 12/1997 | Coucke et al. | 73/595 |
| 5,728,939 A | 3/1998 | Moayeri | 73/595 |
| 5,952,577 A | 9/1999 | Passi | 73/618 |
| 6,029,080 A | 2/2000 | Reynells et al. | 600/407 |
| 6,190,318 B1 * | 2/2001 | Bab et al. | 600/437 |
| 6,244,214 B1 | 6/2001 | Hebrank | 119/6.8 |
| 6,396,938 B1 | 5/2002 | Tao et al. | 382/110 |
| 6,424,857 B1 | 7/2002 | Henrichs et al. | 600/431 |
| 6,644,122 B2 * | 11/2003 | Borowczak et al. | 73/602 |
| 6,722,201 B2 * | 4/2004 | De Baerdemaeker et al. | 73/627 |

* cited by examiner

ULTRASOUND QUALITY INSPECTION OF AVIAN EGGS

CROSS-REFERENCE TO RELATED APPLICATION(S)

This application is a continuation-in-part of U.S. patent application No. 10/076,035, filed Feb. 14, 2002, which claims the benefit of U.S. Provisional Application No. 60/269,281, filed Feb. 16, 2001, which are incorporated herein in full by reference.

BACKGROUND OF THE INVENTION

1. Field of the Invention

The invention relates to non-invasive inspection of avian eggs to make a quality finding and, more particularly, using ultrasound inspection of avian eggs to make a quality finding such as fertility or viability or of other indicia of relative usability, and in consequence of the finding sorting the eggs in at least two and preferably three or more categories.

A number of additional features and objects will be apparent in connection with the following discussion of preferred embodiments and examples.

2. Prior Art

It is known to use nuclear magnetic resonance imaging (MRI) of avian eggs to make a sex and possibly fertility determination. U.S. Pat. No. 6,029,080—Reynnells et al. However the process of nuclear magnetic resonance imaging (MRI) of avian eggs to make a non-invasive determination of any kind will be beset with problems.

The MRI equipment requires a very high capital investment and has unproven reliability. The economics of egg producing operations do not allow purchase of a back up system or expensive components in case of failures of the main system. The MRI equipment is stationed to catch eggs in transit during egg transfer operations. Egg transfer operations cannot be idled for even thirty (30) minutes or else thousands to tens of thousands of eggs will spoil.

The MRI image is in fact a virtually perfect slice of the egg through a given plane. However, the internal structures that allow a sex or fertility determination are hard to make out in such a perfect slice. Indeed U.S. patent of Reynnells et al. discloses quite distinctly how the egg must be oriented in a just so orientation, and then multiple images are taken on 0.5 mm spacings (ie., 50 slices per inch). After that, the best slice has to be determined because next, analysis requires finding a reference marker (eg., eyes or eye sockets) away from which origin a succeeding finding of the sex marker is paced.

Correspondingly, not only must an image from an optimum plane be obtained, the image must be analyzed for subtle features. Just as humans can be trained to develop the right "feel" for vent sexing poults, humans might develop an "instinct" for when all the right combination of factors in a given MRI image suggest a given determination. But human analysis is unfeasible for lack of speed. Computers, though inherently speedy, lack instinct. Computers are far less reliable than humans at making determinations based on subtle factors. Harvard professor Stephen Jay Gould has quipped that to date "artificial intelligence" has yet to obtain merely the level of a cockroach.

It is reported that the MRI process requires cooling the eggs temporarily until the images are obtained. Eg., U.S. Pat. No. 6,029,080—Reynnells et al. Seasoned egg production workers are skeptical of that. Long custom has been to keep eggs in a carefully regulated environment of controlled warmth and humidity. Also, the nuclear MRI radiation just might be worrisome as a death ray to the germ of fresh eggs from the brood farm.

If egg production operations would consider adopting MRI techniques, they'd next have to face paying MRI certified operators at pay scales really unfamiliar in the egg production world.

In sum, the MRI process appears to be an ivory tower solution to a down and dirty problem. State of the art brood farms are known to produce a million (1,000,000) eggs a day. Yet margins are razor thin. The requirement for reliability in the methods relied on is paramount.

The investment in an MRI inspection process costs top dollar. Yet if the MRI inspection equipment goes out then the whole efficiency of the operation is impeded. If an MRI apparatus including its coil went down, it would simply have been cost prohibitive to own a back up in case of failures. There would be no reserve equipment to switch to or change out to in case of failures.

Given the foregoing seasoned veterans are skeptical of the feasibility of nuclear magnetic resonance imaging in poultry operations. The technology appears best left in hospitals where the throughput rate might be one to ten (1 to 10) patients an hour rather than millions of eggs a day.

Nevertheless, efficiency and optimization are paramount in poultry operations. Accordingly, poultry operations would benefit from any reasonably cost-justifiable method for culling poor unqualified eggs from the process stream at opportune times, such as during transfer from brood operations to hatchery operations.

What is needed is an improvement in culling unqualified eggs which overcomes the shortcomings of the prior art.

SUMMARY OF THE INVENTION

It is an object of the invention to oscillate the shell of avian eggs to make a finding of shell quality.

It is another object of the invention to correlate the finding of shell quality to egg quality in terms of fertility or hatching or hatchling viability, or else in terms of any other usability criterion.

It is an additional object of the invention to oscillate the shell of avian eggs by means of acoustic energy.

It is an alternate object of the invention to oscillate the shell of avian eggs by means of a source of ultrasound.

It is a further object of the invention to detect such shell oscillations by means of a detector of ultrasound.

These and other aspects and objects are provided according to the invention in a method and apparatus for determining whether avian eggs are qualified or unqualified for a premium quality based on shell characteristics. The preferred method in accordance with the invention comprises the steps of providing a plurality of the eggs, oscillating the shell of each egg by a source of ultrasonic waves to produce such a signal from the shell oscillation that is detectable by a detector, and then determining whether the egg is qualified or not from analysis of the signal.

Preferably the detected signal is manipulated into a profile comprising detected signal strength versus time. This profile comprises an information portion that is analyzed for a positive indication of premium grade that is preferably characterized by at least one sufficiently steady and strong peak. The analysis of the detected more preferentially comprises integrated response (IR) analysis of the detected signal's strength versus time values.

Optionally, the profile's information portion is analyzed for either or both a positive indication of premium grade, which as before is perhaps characterized by at least one sufficiently steady and strong peak, and/or a negative indication of premium grade that is characterized by relatively unsteady and weak signals across the width of the information portion.

In general, the positive indication of premium grade is correlatable to egg shell quality. In turn, egg shell quality is associated with a quality determination of the avian egg as a whole in terms of relating to fertility or hatching or hatchling viability as well as, in the alternative, being of sufficient quality for human consumption.

The foregoing is advantageous for poultry including turkey farms having hatchery operations because the eggs sorted into the premium grade are graduated to hatchery operations. The other eggs are removed and either discarded or perhaps sorted for alternative other use such as pet consumption.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 3 is a graph obtainable from a display of a signal analyzer (eg., for processing the output of the detector of FIG. 1), wherein the graph shows a profile of detected signal strength versus time for the special case of the source signal transiting across the gap to the detector without interposition of any object therebetween especially an egg (ie., therefore just through air), whereby the graph illustrates an example reference profile of detected signal strength versus time for such base factors as present air temperature and humidity as well as among various other things the distance of the gap between the transducers; such profiles in general consequently allowing analysis for such values as time-of-flight or velocity of the source signal, an integrated response of a selected peak or alternatively an integrated response across a selected bandwidth and so on;

FIG. 7 is a block diagram flow chart of the method in accordance with the invention for providing ultrasound quality inspection and sorting of avian eggs, wherein the quality determination comprises any of fertility, viability or other usability; and, FIGS. 8 through 25 comprise a series of views showing alternative combinations of transducers and egg-orienting devices for accomplishing various objects of the invention, albeit for convenience in the views the latter devices predominantly comprise suction-cup type devices, wherein:

DETAILED DESCRIPTION OF THE PREFERRED EMBODIMENTS

Figure 1:
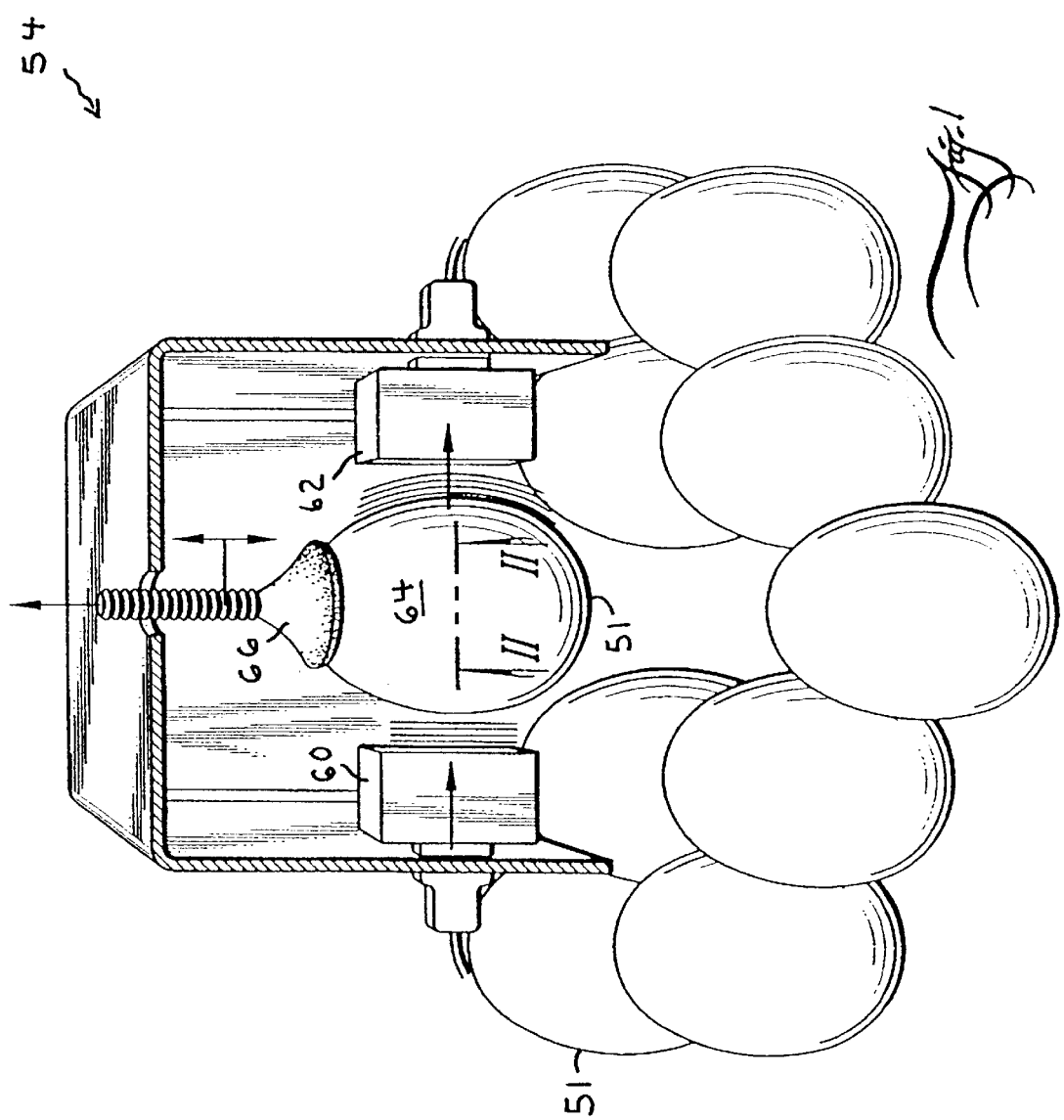
FIG. 1 is a perspective view of an apparatus for ultrasound quality inspection of avian eggs in accordance with the invention, wherein a given egg is disposed between a source and a detector of ultrasonic energy, the detected signal obtained thereby allowing analysis to make such a quality finding as fertility, viability or other relative usability.

FIG. 1 shows an apparatus 54 for ultrasound quality inspection of avian eggs 51 in accordance with the invention, and as arranged in a preferred manner of operation.

The assumptions which underpin the inventive apparatus and method are, briefly, as follows. Ultrasonic energy is used to "ring" an egg 51 like a hammer tap rings a bell. The ringing egg is listened to. If the egg rings clear and strong in one or two or more characteristic modes of oscillation, the shell is reckoned as being of good quality. If not or, that is, if the egg clangs like an old metal platter dropped on the floor, the shell is reckoned as being of poor quality.

Importantly, the quality of the shell is reckoned as an indication of quality of hatchling viability. It is considered that poor shell quality is a symptom of various bad causes or bad indicators. To list a few, it is reckoned that poor shell quality indicates a cracked shell, or one compromised by (undue) micro-fractures, an overly porous shell, or an especially thin shell. Undue problems in such matters as cracks, micro-fractures, porosity and/or shell thinness are likely indicative that the shell is probably an unsuitable barrier to diseases and contaminants. It is known that poor shell quality allows diseases to enter and incubate inside the egg. These diseases like salmonella and mycoplasma spread from hatchling to hatchling when the bird emerges from the shell. Also, undue problems in matters of cracks, micro-fractures, porosity and/or shell thinness are likely indicative that the shell is probably an unsuitable container of moisture. Sometimes a bird hatches "pip alive" but dies in the struggle to get out of the shell or soon after. A frequent cause of this is weakness from dehydration.

More speculatively, it is also reckoned that poor shell quality could also be an indication if the blastoderm is already or nearly dead. The life of the blastoderm sustains the growing process of the egg as a whole including, presumptively, the health of the membrane lining the shell as well as even possibly the integrity of the shell in matters as absence of undue thinness or porosity and so on. Again, too much porosity is bad because the egg contents are then vulnerable to dehydration among other things.

To return to FIG. 1, it shows a pair of non-contacting transducers 60 and 62 arranged in opposition to each other. Non-contact ultrasound is highly preferred so as to avoid a liquid couple between the transducers and shell 64. It is feared that any liquid couple will cause intolerable problems. The non-contact probes do not subject the egg to any more harmful elements than already present in the controlled environment of brood, transfer and/or hatchery operations. The ultrasonic energy is transmitted from point to point. One transducer 60 serves as the source relative to its opposite number which serves as the detector 62. Example transducers suitable for the purpose include without limitation model nos. NCT 102 transducers of SecondWave Systems, Inc., State College, Pa., which transducers are characterized as nominally operating on a 200 kHz frequency and having a planar 25 mm active area diameter.

Figure 7:
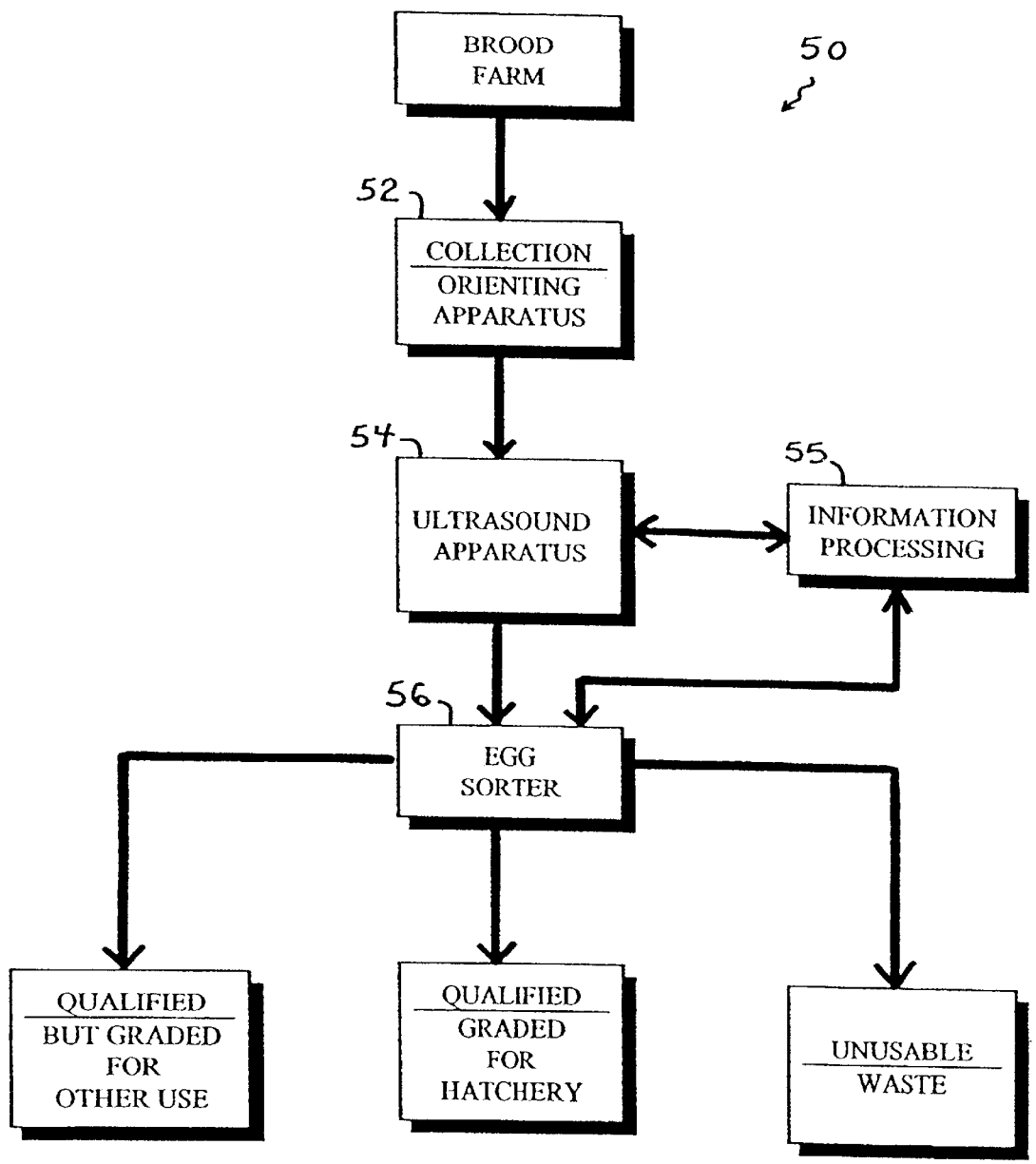

Not shown in FIG. 1 (but indicated generally as portions of one or more blocks 54 and 55 in FIG. 7) is a signal analyzer which is utilized for among other things processing the feed and detected signals of the source 60 and detector 62 respectively. An example non-contact ultrasound signal analyzer suitable for the purpose includes without limitation model no. NCA-1000-2En also of SecondWave Systems, Inc., State College, Pa. Given the foregoing, an egg 51 is disposed between the source 60 and detector 62 for an ultrasound quality inspection in accordance with the invention. Whereas the egg 51 is shown suspended by its pointed end from an inverted suction cup 66, the egg 51 could be supported in alternative other fashions without limitation.

FIG. 1 shows the source transducer transmitting a beam of ultrasound energy that slams into one side (or the left side given the perspective of FIG. 1) of the egg 51. In a typical arrangement with the above-identified transducers, the source and detector might be space 11 cm (4⅓ inches) apart. It is fairly well estimated that about 99.9% of the source energy is reflected by the egg shell 64 because of, in technical language, the mismatch between the acoustic impedance of air and the shell 64. On the opposite side (or right side given the perspective of FIG. 1) of the egg, the detector 62 is listening for those components or portions of the source energy that reach it.

Figure 2:
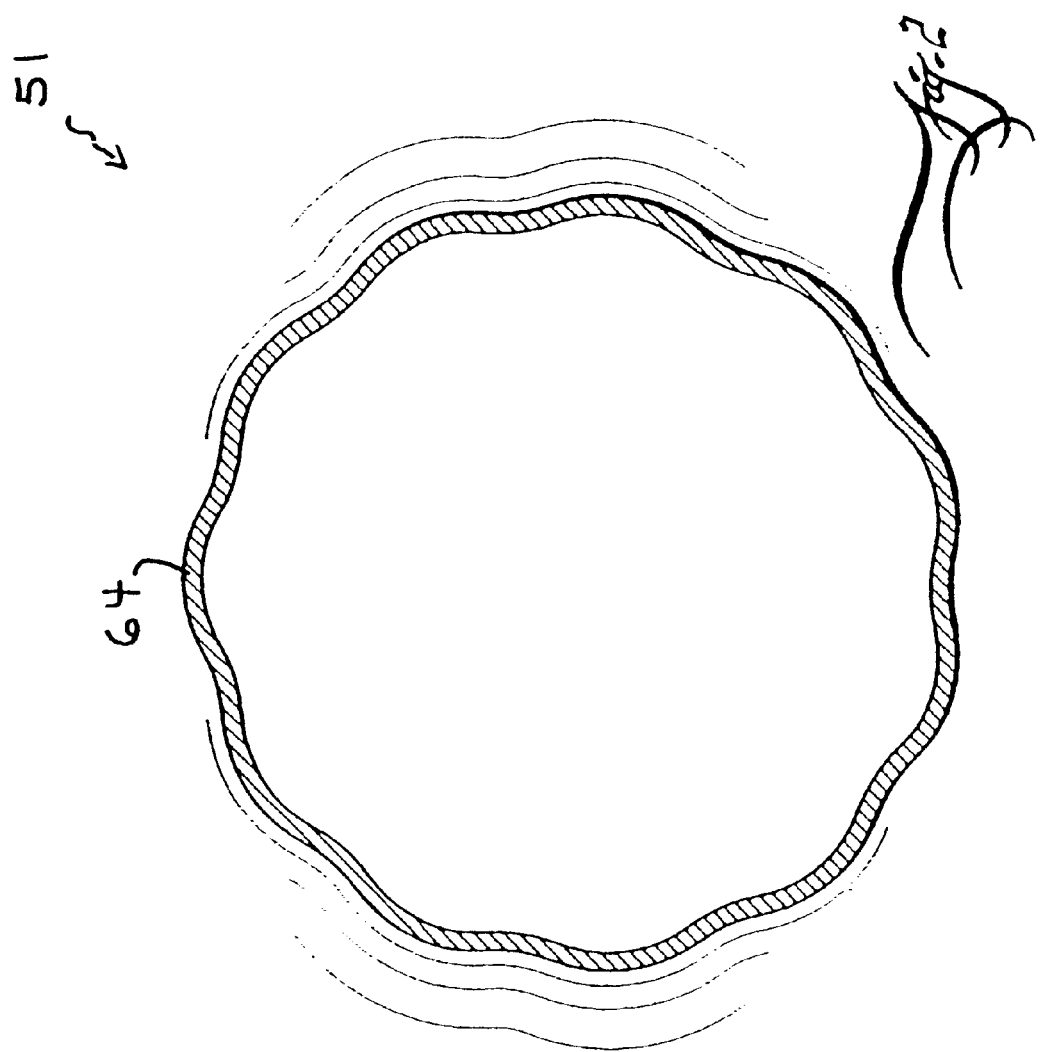
FIG. 2 is an enlarged sectional view taken along line II—II in FIG. 1 and which illustrates oscillations induced in the egg shell by the source transducer, wherein the distortion in the egg shell is illustrated on a gross scale for visual emphasis only.

FIG. 2 is a depiction for convenience of illustrative purposes only presumptively showing the dynamic oscillations induced in the shell 64 by the source signal. The egg shell 64 vibrates or oscillates somewhat as shown, although clearly not on such a gross scale as drawn, according to one or more characteristic modes of oscillation. See, eg., A. H. Benade, "Fundamentals of Musical Acoustics" (New York: Dover 1991). The shell 64 comprises a surface which is, needless to say, ovoid shaped. Sometimes in more general terms (but technical language nevertheless) the shell is reckoned as a prolate spheroid, or that is that shape obtained by rotation of an ellipse about its major axis. Presumptively the shell will have modes of oscillations simulative or characteristic to transit around its "equator," or the hoop through which cutting line II—II is taken. In addition, the shell 64 surface will presumptively also have modes of oscillation characteristic to circumnavigation transit around its poles. FIG. 2 provides illustrative depiction of wave energy transiting around the equator of the egg 51 as suspended in FIG. 1.

Figure 3:
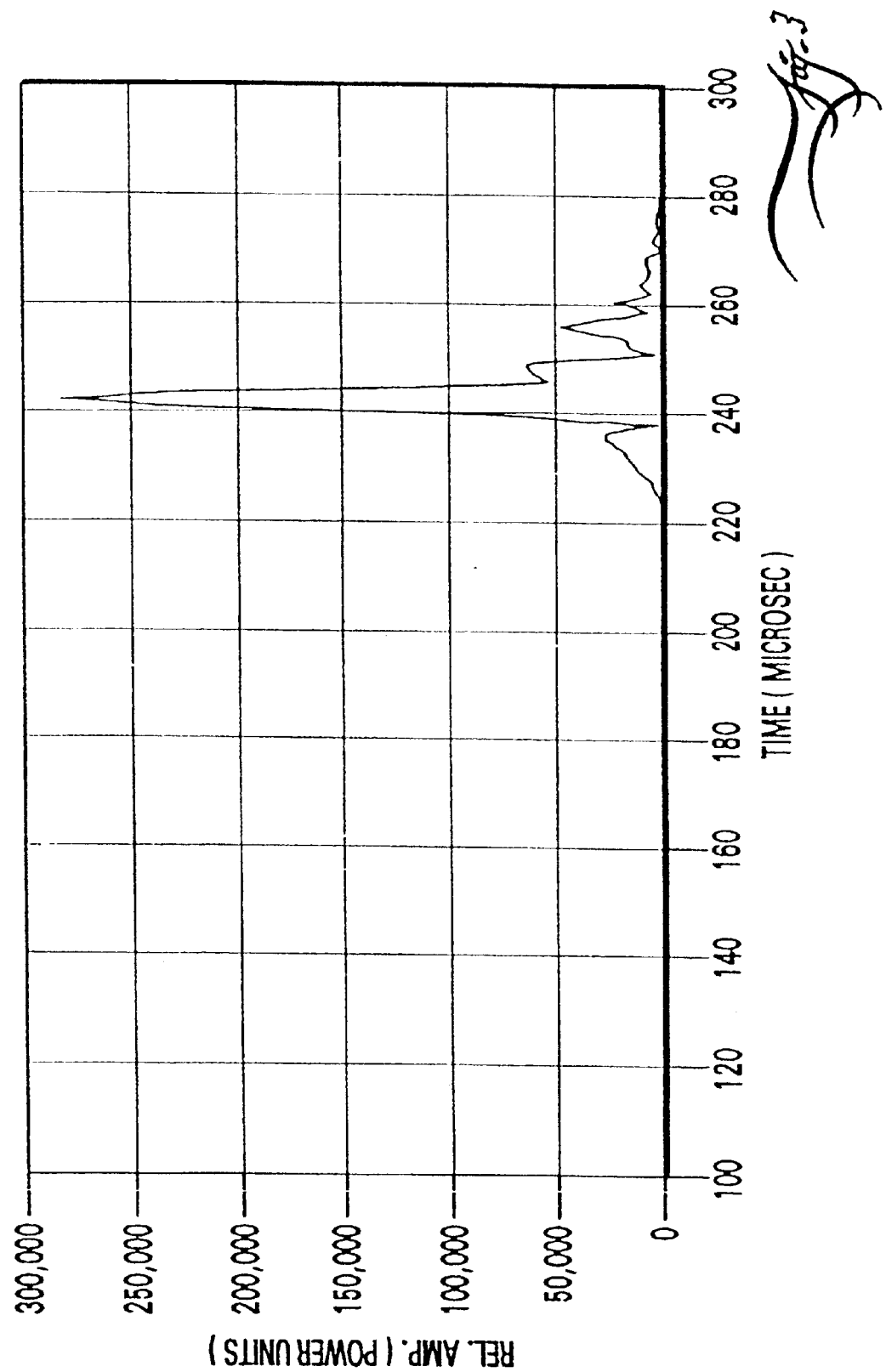
Figure 4:
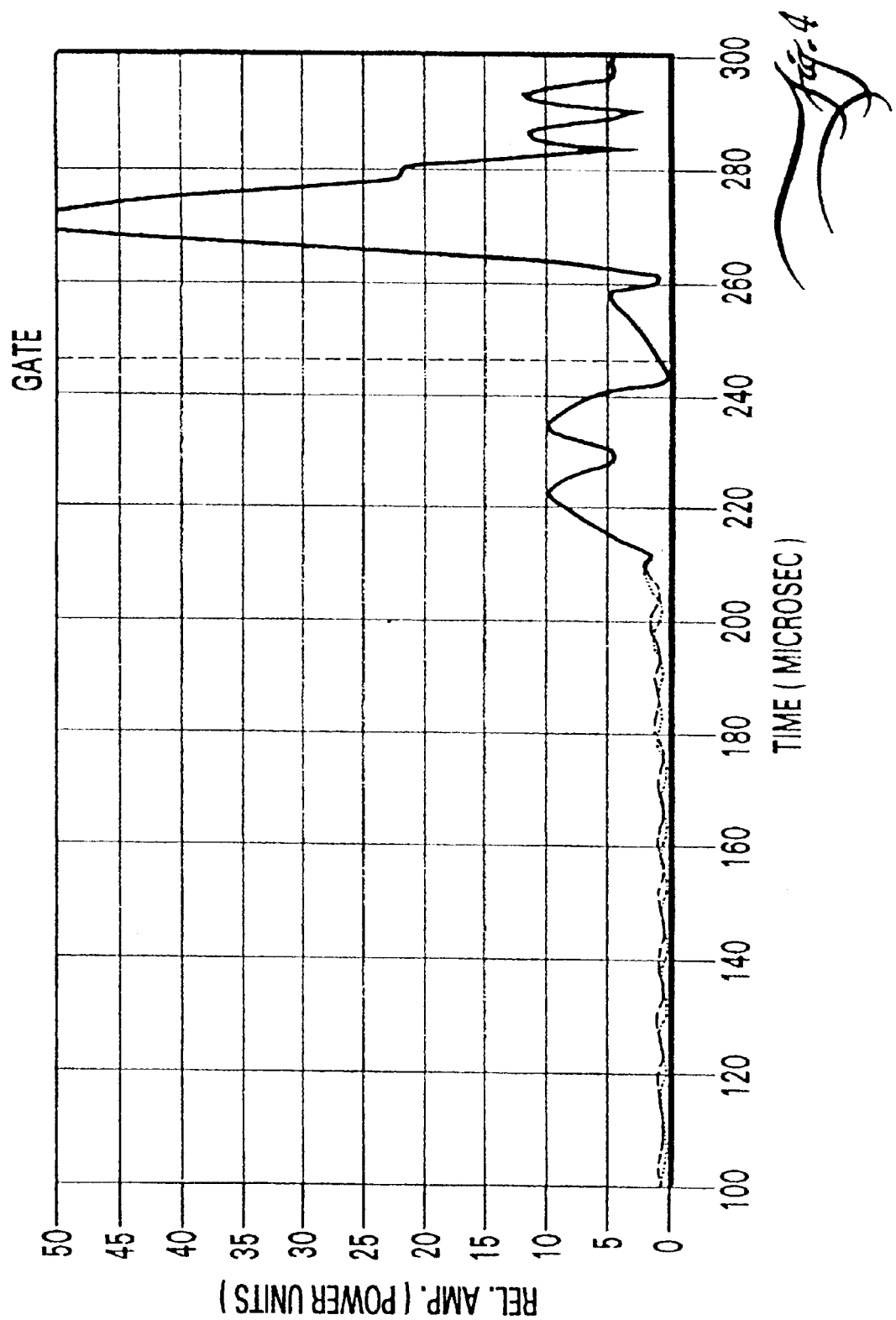
FIG. 4 is a comparable graph except showing an example profile for the representative case of a quality egg interposed between the source and detector, wherein even though the source signal's strength is diminished by greater than 99.9%, the information portion of the detected signal (ie., to the left of the gate) appears to ring strong and steady on at least one or two characteristic peaks.
Figure 5:
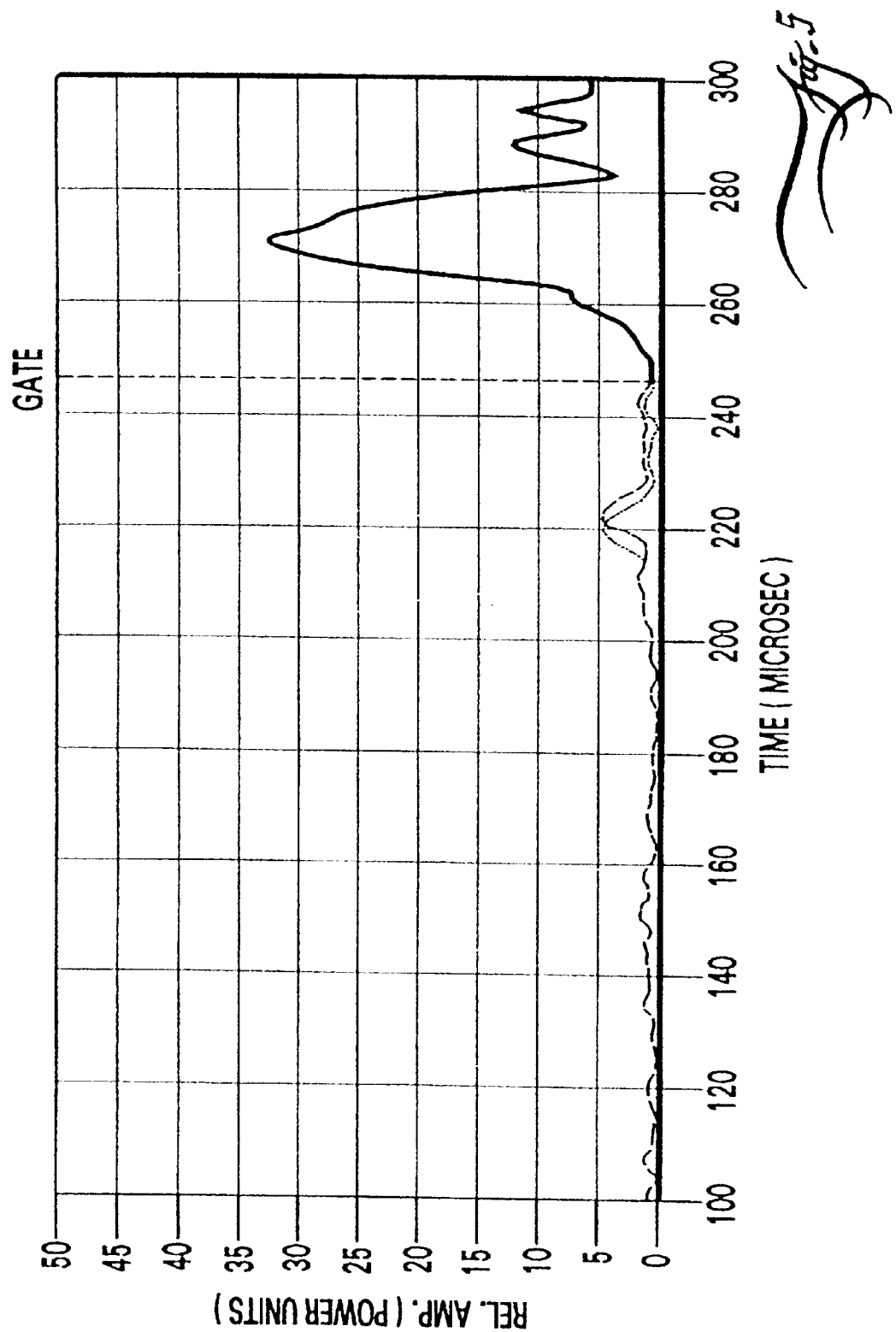
FIG. 5 is a graph comparable to FIG. 4 except showing for contrast an illustrative case of an unqualified egg interposed between the source and detector, wherein not only is the source signal's strength diminished by greater than 99.9% but also the information portion of the detected signal (ie., to the left of the gate) is weaker and appears to clang unsteadily.

FIGS. 3 through 5 are series of comparable views of graphs. Each graph shows a profile of detected signal strength versus time. FIG. 3 shows a graph of a set-up test in the absence of an egg. FIG. 4 shows one representative example profile of a good quality egg. FIG. 5 shows one representative profile of an unqualified egg.

Preliminarily, the judgements of whether egg and/or egg shell quality is good or bad, or qualified or unqualified, were obtained through trials with actual eggs. Batches of eggs were inspected by the above-described non-contact ultrasound equipment and results were recorded. Some eggs were immediately broken open for examination of the contents including the blastoderm for such visual determinations as alive and healthy, deformed, dead or near death and so on. Other eggs were marked and tracked for observations through hatchery operations up to hatching, if that occurred, and then continuing on with the emerging poult for about six days after. The findings of that experience are graphically shown in part by FIG. 6.

To turn to FIG. 3, it is a graph obtainable from a display of the above-described signal analyzer. Generally the signal analyzer can be reckoned in many ways as PC computing system. The display comprises an attached monitor and the graphs shown in FIGS. 3 through 5 hereof are simulative of screen print-outs. The FIG. 3 graph shows a profile of detected signal strength versus time for the special case of the source signal shooting across the gap to the detector without interruption by an object such as an egg. The graph therefore illustrates an example reference profile of detected signal strength versus time for such set-up factors as the current air temperature and humidity as well as among various other things such as the distance of the gap between the transducers. This profile allows analysis of very basic values such as time-of-flight or velocity of the source signal and diminishment of the source signal across the gap.

FIG. 4 shows a comparable profile except being a representative example of what is obtained for a quality or qualified egg. As matter of general interest, about 99.9% and more the source signal's strength is diminished. Much of the source signal's energy is reflected by the shell where the source signal originally slams into the left side of the egg (ie., left according to the perspective of FIG. 1). That much which is detected by the detector produces a profile as shown by FIG. 4 in the typical case of a quality or qualified egg. The twin peaks appearing in the information portion of the detected signal (ie., to the left of the gate) provide steady strong signals. In essence, the egg shell appears to ring strong and steady on at least one or two characteristic peaks. The portion of the profile to right of the gate is noise. It might comprise echos of the source signal as scattered about by the environment. The profile of FIG. 4 permits various techniques of analysis including without limitation an integrated response analysis of one selected peak, or alternatively an integrated response across a selected bandwidth as encompassing two peaks and so on.

In contrast, FIG. 5 shows an illustrative case of an unqualified egg. In FIG. 5, the information portion of the detected signal (ie., to the left of the gate) is weak and unsteady all across the spectrum. At least one peak is apparent but it is unsteady and appears to dance on the screen. Indeed the peak dances left and right and might grow and recede in very quick time. Such a nub of a peak that dances so does not allow close integrated response analysis because the values are evidently too unsteady to average. One way to reckon the behavior of an unqualified egg is that the detected signal appears to "clang" unsteadily and not ring true and strong, something akin to the clang of a cheap metal tray dropped on the floor.

Figure 6:
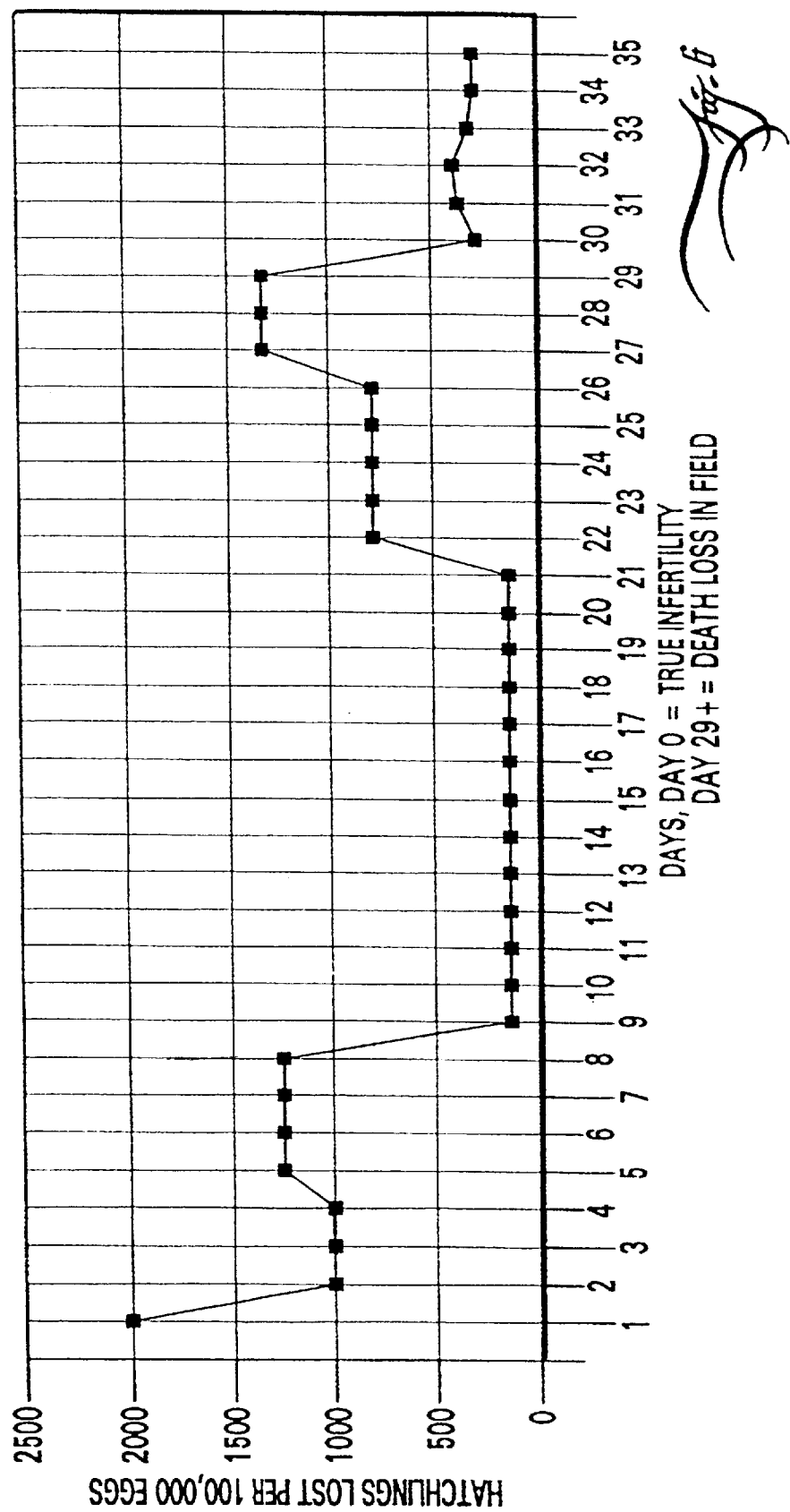
FIG. 6 is a graph showing a profile of hatchlings lost (per 100,000 eggs) versus time based on data pertaining to turkey operations.

FIG. 6 as mentioned previously is a graph showing a profile of hatchlings lost (per 100,000 eggs) versus time based on data pertaining to turkey operations. Day 29 represents ordinary hatching time. Between day 0 and day 29 the profile has a bathtub shape. Presumptively the steeply dropping original part of the profile represents cases of dead, dying or deformed blastoderm due to matters present from the start. The steeply climbing part of the curve approaching day 29 is presumptively due to matters such as contaminated, diseased or dehydrated eggs. Days 28 through 30 might roughly correspond to "pip alive" deaths, or pips too weak to struggle out of the egg shell or terminally failing immediately thereafter. Days 31 through the end of the record generally correspond to hatchlings emerging dehydrated or diseased and otherwise too unhealthy too persist.

It is an aspect of the invention that problems with eggs and hatchlings through about day 35 (ie., the sixth or so day after expected hatching time) can be reasonably determined from an ultrasound quality inspection in accordance with the invention taken during the transfer operation between brood and hatchery operations, or on about day 0. Actual trials support this.

On the other hand, the non-contact ultrasound trials to date have failed to show any correlation between integrated response (IR) measurement and gender of live poults.

FIG. 7 is a block diagram flow chart of a method 50 in accordance with the invention that utilizes ultrasound quality inspection of avian eggs.

Briefly, eggs are collected immediately as practicable at the brood farm after laying. Nowadays while the eggs are transferred from the brood farm to the hatchery they go through an intermediary process where they are washed and sterilized (not shown). The method 50 in accordance with the invention is preferably situated to operate on the eggs before the washing and sanitizing station. Hence in FIG. 7, the eggs are collected and fed to a conveying apparatus 52 as known in the art. FIG. 1 shows the eggs 51 transported in a suitable orientation and in a regular pattern or registry, both of which factors are desirable as more particularly described below.

Referring again to FIG. 7, the eggs are conveyed to an ultrasound station 54. Ultrasound inspection transpires, the results of which are analyzed by an analyzer or processor. The analyzer is configured to make a finding as described above in connection with FIG. 4 by means of an integrated response (IR) analysis of the steady peak or peaks of the information portion of the detected signal.

Generally speaking, in FIG. 4 the first peak in time (eg., at ~222 μsec as distinguished from the peak at ~235 μsec)) has been discovered to most strongly correlate with egg shell quality. Hence the first peak in time might correspond to primary characteristic mode of oscillation whereas the second peak in time might correspond to a secondary mode, although to date this has not been established either way. Nevertheless, the IR analysis correlates one or more quality criterion(ia). The quality findings are preferably utilized for a process to make one of three choices:—namely, that the egg is qualified for passing on through to the hatchery, or alternatively that the egg is not qualified for hatching but is otherwise gradable for other use such as pet food, or else that the egg is unusable and hence waste.

The quality findings obtained by the method 50 in accordance with the invention are shown by trials to correlate to various poor quality factors with egg shells, including things as cracks, micro-fractures, and undue porosity or thinness and so on. These same poor quality factors are also known to correlate to risk of contamination by, for example and without limitation, salmonella. Eggs at risk to salmonella contamination are unusable for most purposes and generally might be graded as waste although alternatively such eggs can be sorted for use by a protein plant or the like.

Returning to FIG. 7, the eggs are sorted based on the findings of the ultrasound station by a sorter 56 which sorts each according to the corresponding finding. Sorting can be accomplished in accordance with various routine ways known in the art. Referring to FIG. 1, the same inverted suction cup which lifts the egg for ultrasound inspection might also be utilized for sorting duties. Alternatively, a successive inverted suction cup (not shown in FIG. 1) might be utilized for this duty or else a carousel and so on. Persons ordinarily skilled in the art could readily devise routine other ways for doing so.

Whereas FIG. 7 shows three dispositions for eggs this is done so merely for convenience in the drawings and the invention is not limited to sorting the eggs into any indefinite number of categories according to given criteria.

Yet in FIG. 7, preferably the premium quality eggs are hatchery quality and this includes being of sufficient quality for human consumption. Correlation results show that such eggs are fertile and have the pre-requisite shell quality to hatch and provide a healthy hatchling through at least the first several days after emerging from the shell. Those eggs which fail the premium quality standards might next be considered if unusable. Unusable eggs are preferably discarded. However, if the egg has an intermediate quality, it remains fit for perhaps other use such as pet consumption and can be sorted for such.

In view of the foregoing, the results of the ultrasound inspection 54 are analyzed by an analyzer 54 or 55 or other information processor or controller 55 to make a finding correlatable to the egg's shell quality. The egg's shell quality in turn is correlatable to such grading factors as grading for fertility or hatching or hatchling viability. In more accurate language, the relationship between egg shell quality and indications of fertility or hatching or hatchling viability might be alternatively referred to as an association. The association between the egg's shell quality obtained from the detected signal of ultrasound apparatus 54 and the grading for fertility or hatching or hatchling viability is accomplished by pre-programmed routines and data stored on and executed by the information processor 55. Such routines and data would be based on the trials previously conducted as well as refined as time extends by further experience with the practice of the method and use of the apparatus 50 in accordance with the invention.

It is an aspect of the invention that the ultrasound inspection is preferably transacted as soon as the eggs are collected from the brood farm. That way, the grading or sorting decision is made as early as possible to extract out the sub-grade eggs before any more resources are expended on them. Accordingly the invention provides advantageous optimization of efficiency especially for high-volume poultry including turkey operations in which optimization and efficiency are paramount.

To turn now to FIGS. 8 through 25, these comprise a series of views showing alternative combinations of transducers and egg-orienting devices for accomplishing various objects of the invention, albeit for convenience in the views the latter devices predominantly comprise suction-cup type devices.

In connection with FIG. 1, it was previously mentioned that non-contacting transducers were highly preferred so as to avoid a liquid couple between the transducers and shell 64. Nevertheless, egg-contacting devices are common in the industry predominantly for purposes of orienting or positioning the eggs into an examination position. Indeed FIG. 1 does show a suction-cup pick-up device 66 lifting the egg 51 presumptively up out of a plane of a transport container or conveyor. Recognizing that qualified contacting devices will be allowable by the industry despite stringent contamination-elimination controls, it is an aspect of the invention to incorporate some arrangements of contacting devices with the inventive purposes of targeting a source and detector of ultrasonic energy at the egg 51. Accordingly, FIGS. 8 through 25 represent a non-exclusive compilation of alternative other ways to accomplish the objects of the invention.

Figure 8:
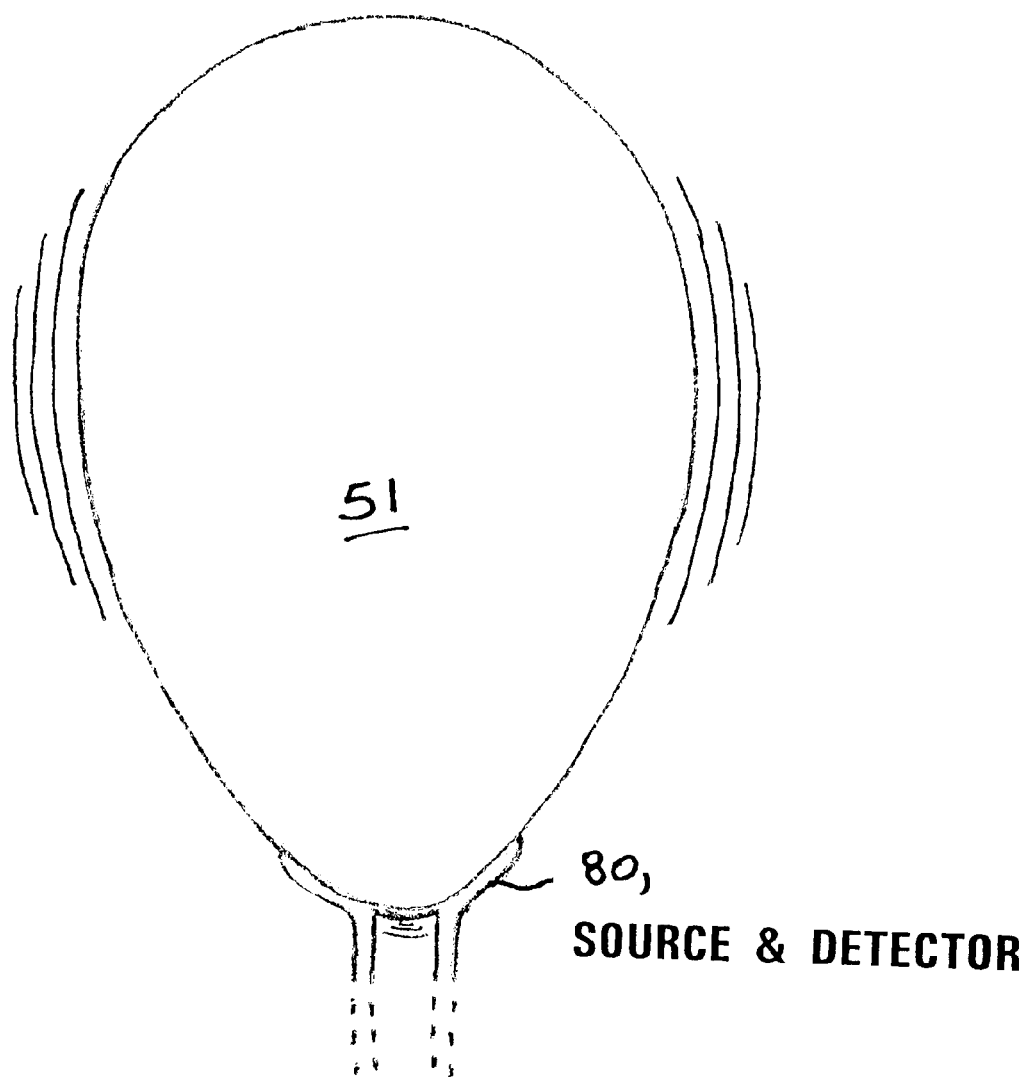
FIGS. 8 though 23 are all elevational views.

FIG. 8 is an elevational view showing an up-stroke contacting device 80 incorporating a transducer performing both source and detector functions. The contacting device 80 contacts the vertically-oriented egg 51 on the egg 51's downward-oriented pointed end, away from the large end where the air cell is found.

Figure 9:
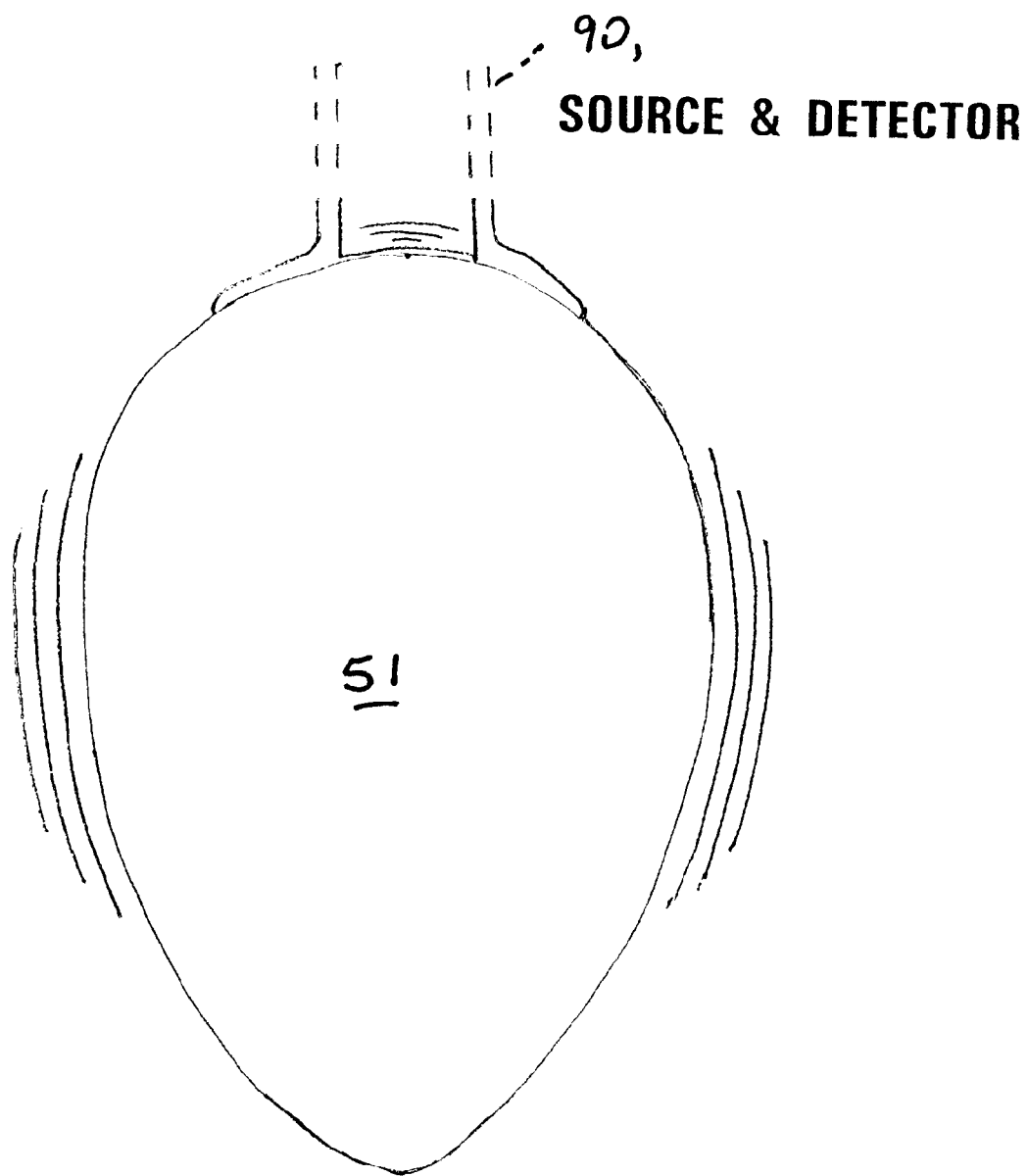

FIG. 9 is a comparable elevational view except showing a down-stroke contacting device 90 incorporating a transducer performing both source and detector functions. This contacting device 90 contacts the vertically-oriented egg 51 on its upward-oriented large end, which indeed is where the air cell is found.

Figure 10:
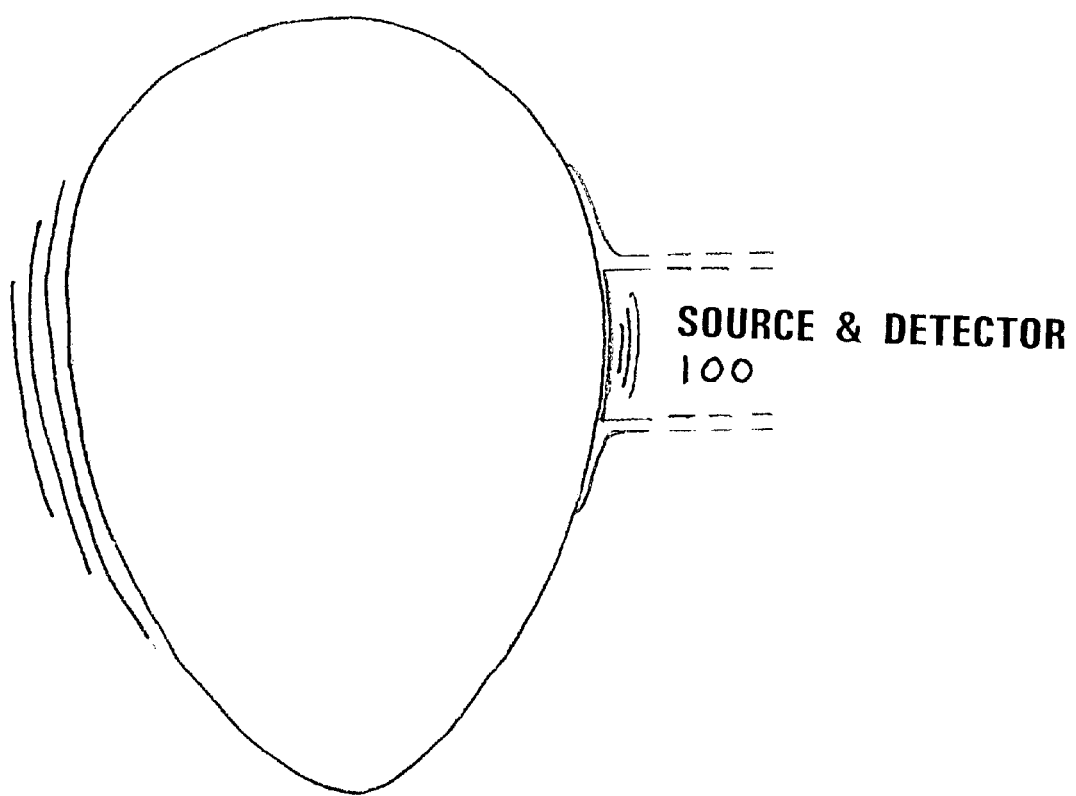

FIG. 10 is another comparable elevational view except showing a side-stroke contacting device 100 likewise incorporating a transducer performing both source and detector functions. This contacting device 100 contacts the vertically-oriented egg 51 on its side or, more accurately, equator and whereas the view show the egg oriented with large end upward, this is shown that way for convenience in the drawing and as the egg can be readily oriented various other ways, vertically or horizontally, so long as the contacting device 100 reaches for a target approximately on the egg's equator.

Figure 11:
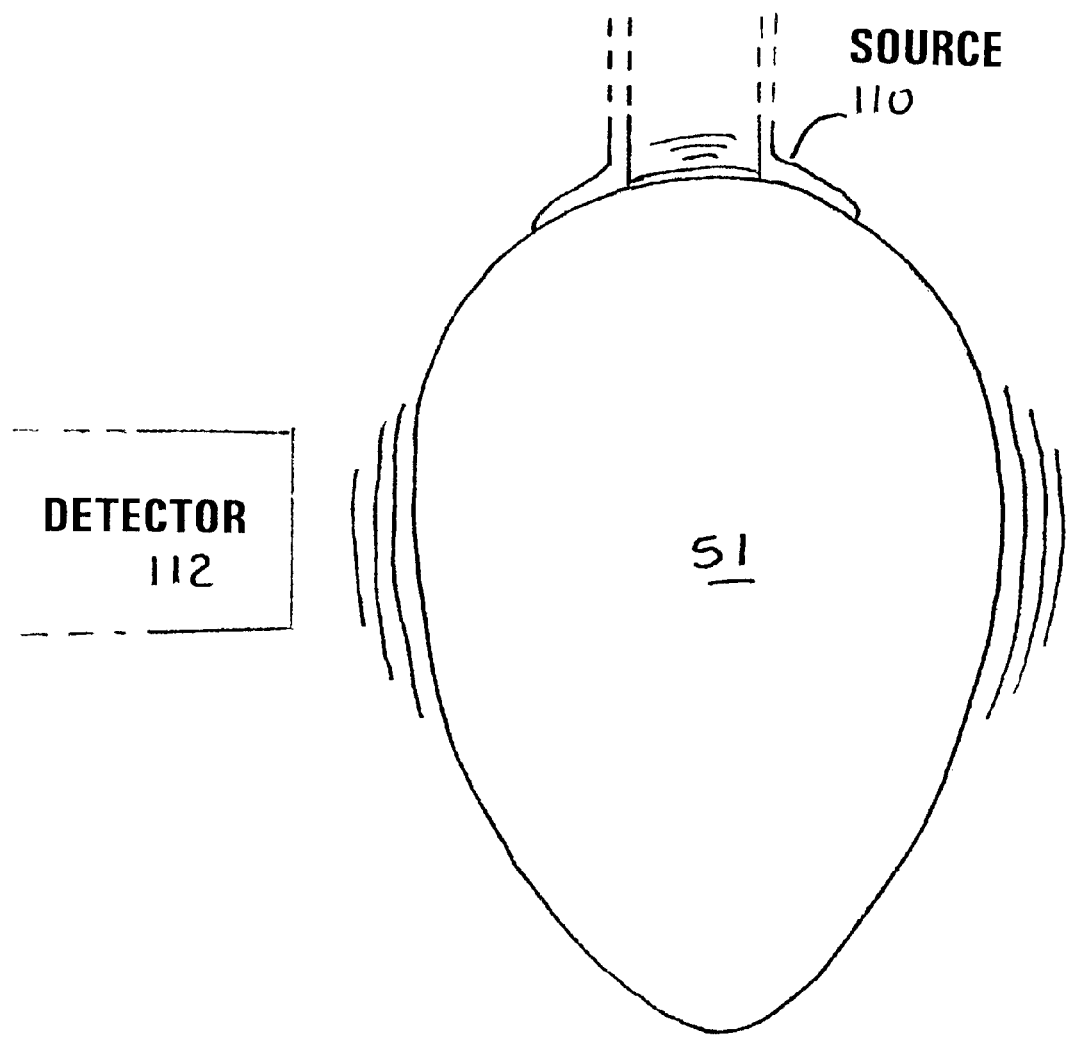

FIG. 11 is an elevational view showing a down-stroke contacting device 110 incorporating a transducer performing just source functions, and in which view the contacting device 110 reaches for the vertically-oriented egg 51's large end. This arrangement utilizes a separate, non-contact detector 112 which in this view is not opposite the source 110 but on axis perpendicular to it. Hence the source 110 is impinging the egg on an end (in this view, the large end) as the detector 112 is detecting signals more strongly emanating from the egg 51's equator.

Figure 12:
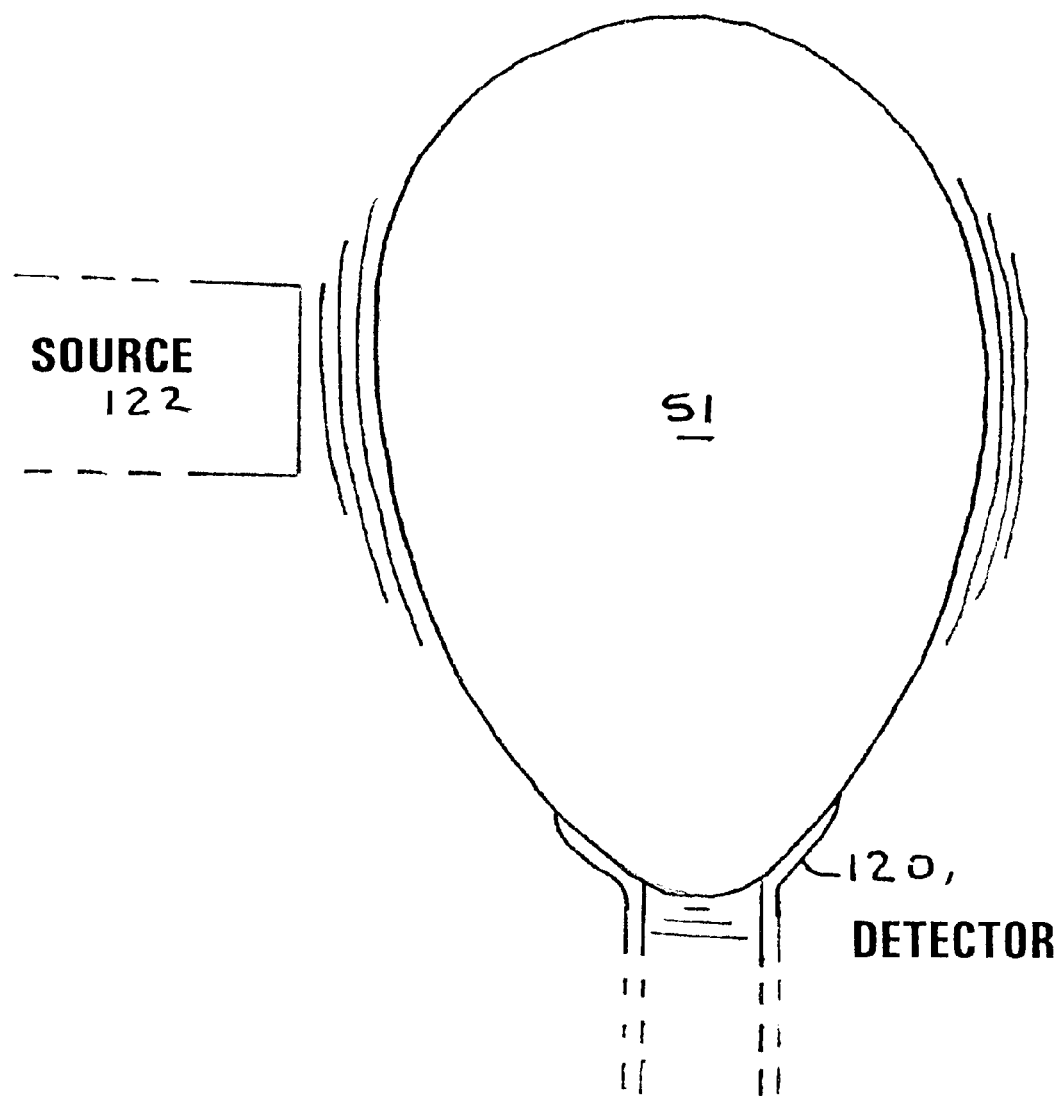

FIG. 12 shows an alternative variation on FIG. 11 wherein an up-stroke contacting device 120 incorporates a transducer performing just detector functions. The detector/contacting-device 120 reaches for the vertically-oriented egg 51's pointed end. A separate, non-contact source 122 is oriented on an axis perpendicular to the detector 120 to detect signals more strongly emanating from the egg's equator.

Figure 13:
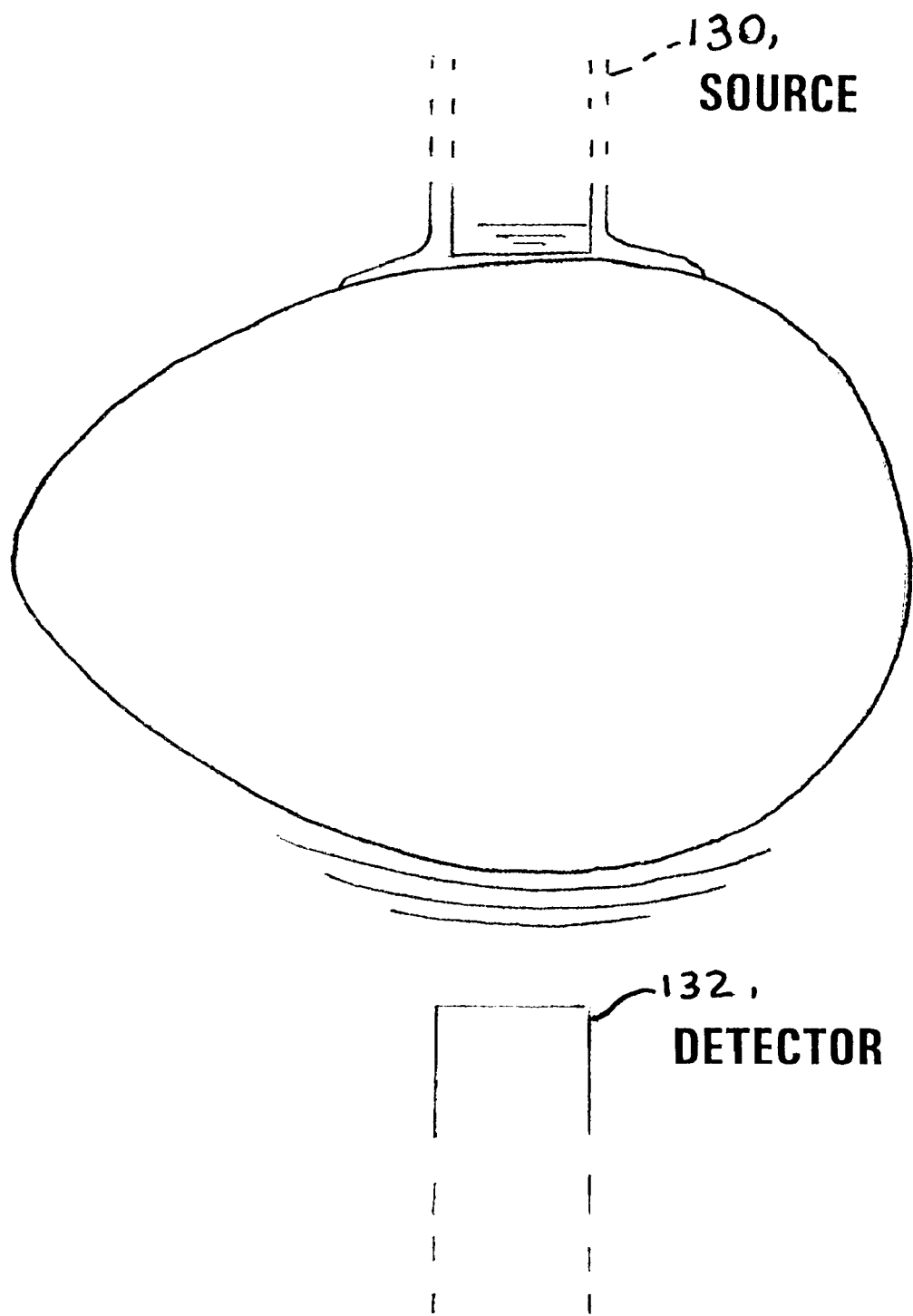

FIG. 13 is an elevational view which in contrast to the foregoing shows a horizontally-oriented egg 51, or that is lying on its equator with its long axis extending horizontally. A down-stroke contacting device 130 incorporates a transducer performing source functions as a separate, non-contact transducer 132 performs detector functions. In this arrangement the source 130 and detector 132 are arranged on a common axis and are opposed to each other.

Figure 14:
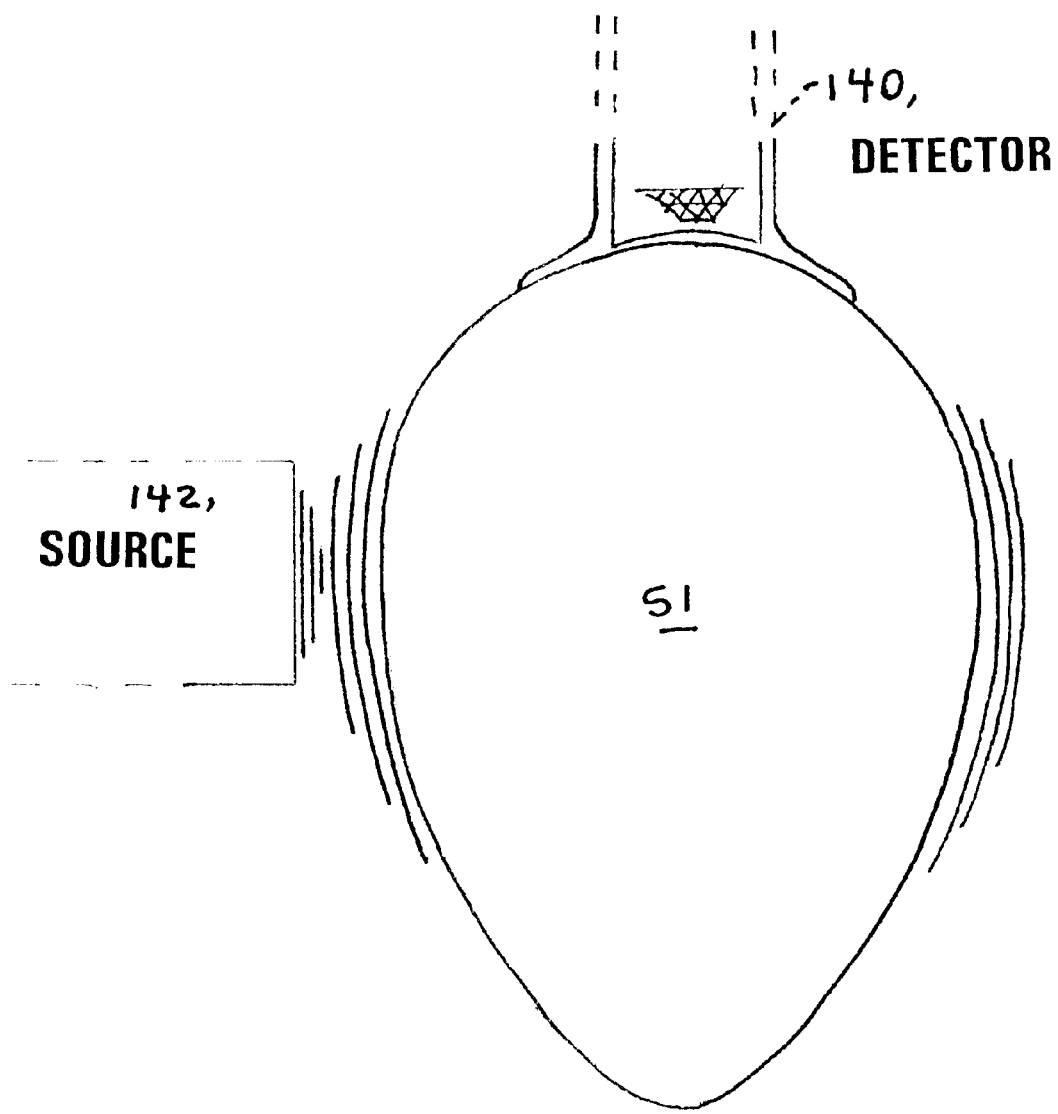

FIG. 14 is an elevational view comparable to FIG. 11 except showing a down-stroke contacting device 140 incorporating a detector transducer as the separate, non-contact transducer 142 performs source functions. The down-stroke device 140 contacts the vertically-oriented egg 51's large end as the non-contact source 142 is aimed at a target on the egg 51's equator.

Figure 15:
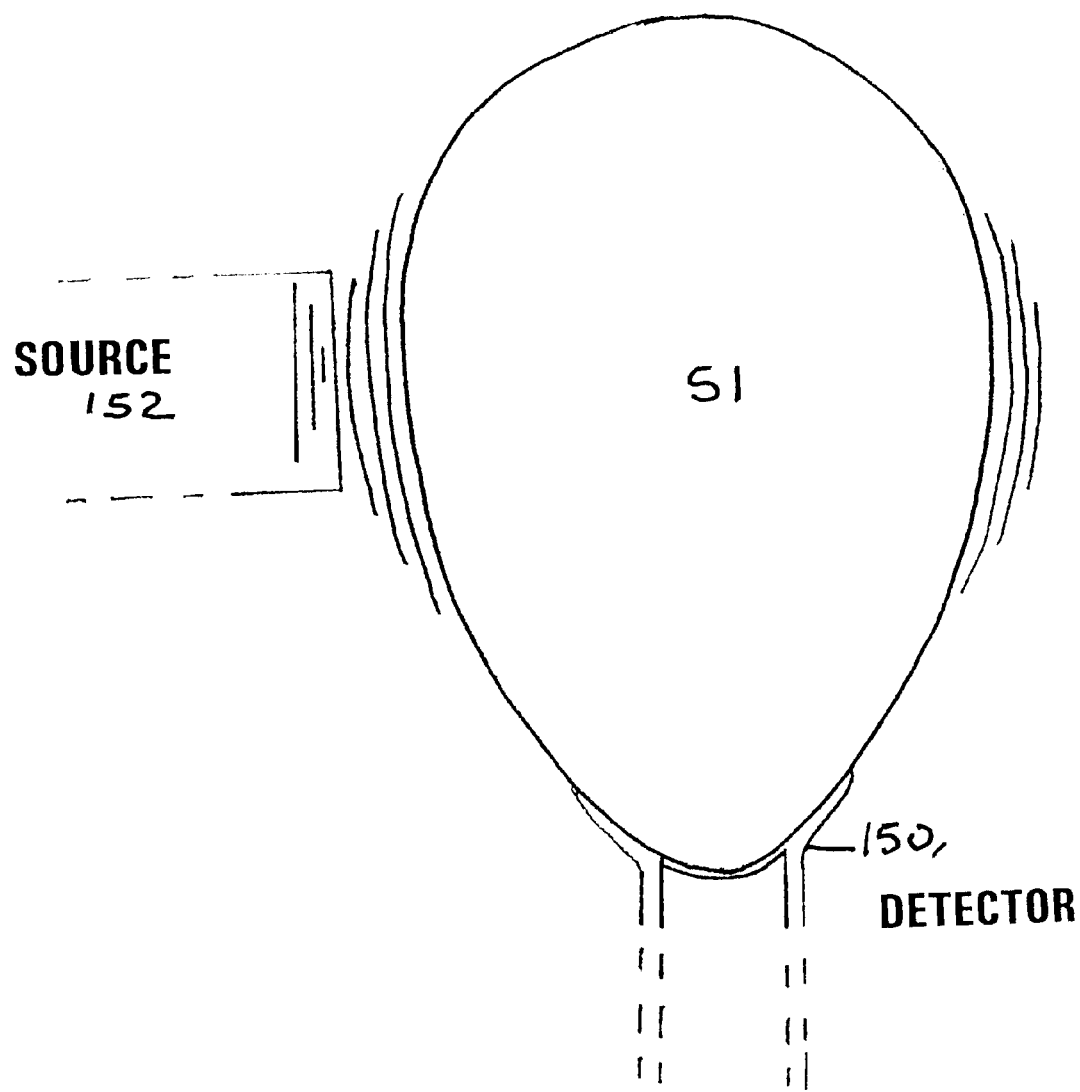

FIG. 15 reverses the position of the detector 150 in that an up-stroke contacting device 150 incorporating a detector 150 reaches for the vertically-oriented egg 51's downward-oriented pointed end. The source 152 comprises a non-contact transducer aimed at a target on the egg 51's equator.

Figure 16:
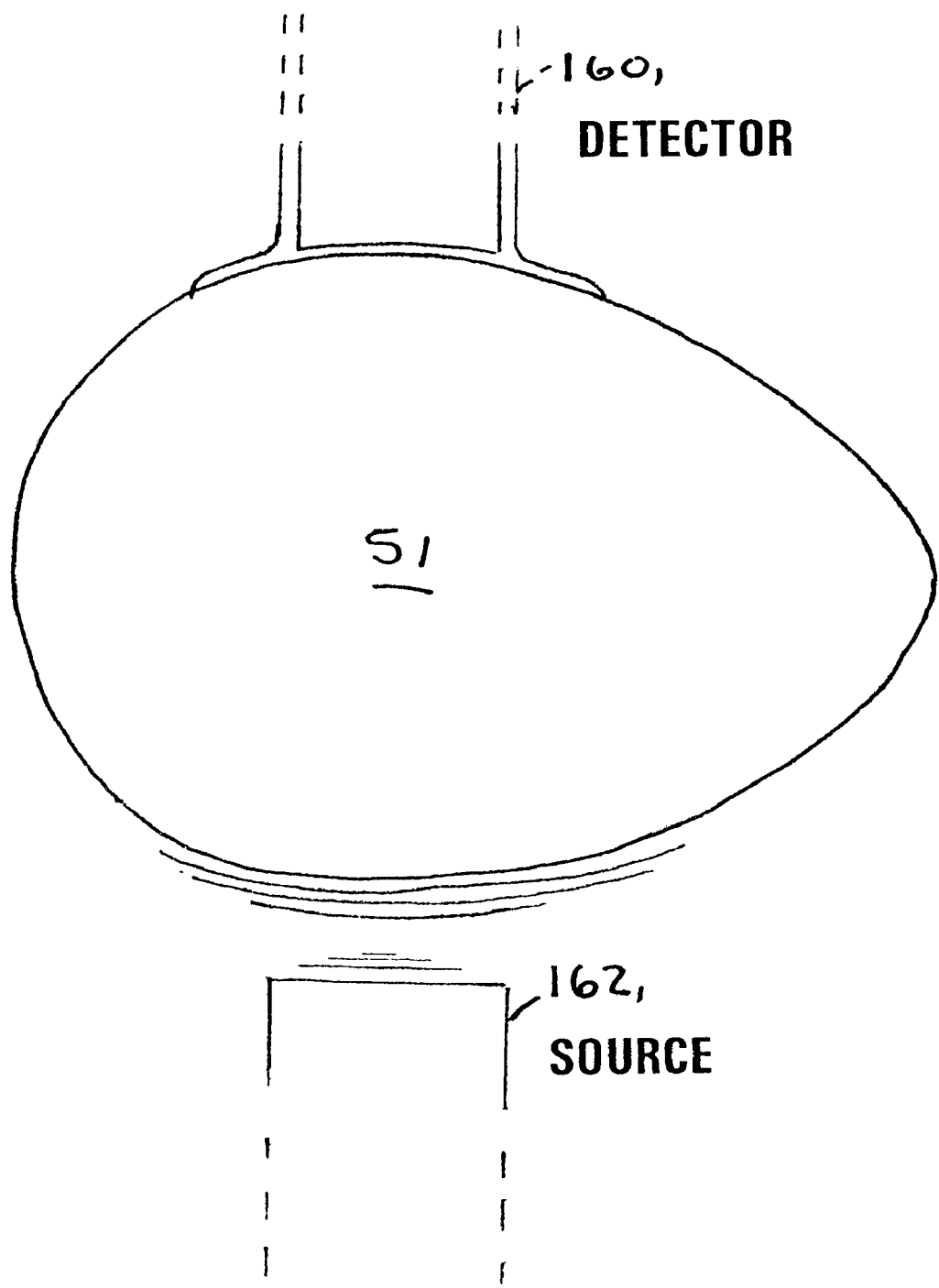

FIG. 16 is an elevational view comparable to FIG. 13 except showing some variations as follows. The egg 51 again lies horizontally, or that is lies on its equator with its long axis extending horizontally. A down-stroke contacting device 160 incorporates a transducer performing detector functions as a separate, non-contact transducer 162 performs source functions. In this arrangement the detector 160 and source 162 are arranged on a common axis and are opposed to each other.

Figure 17:
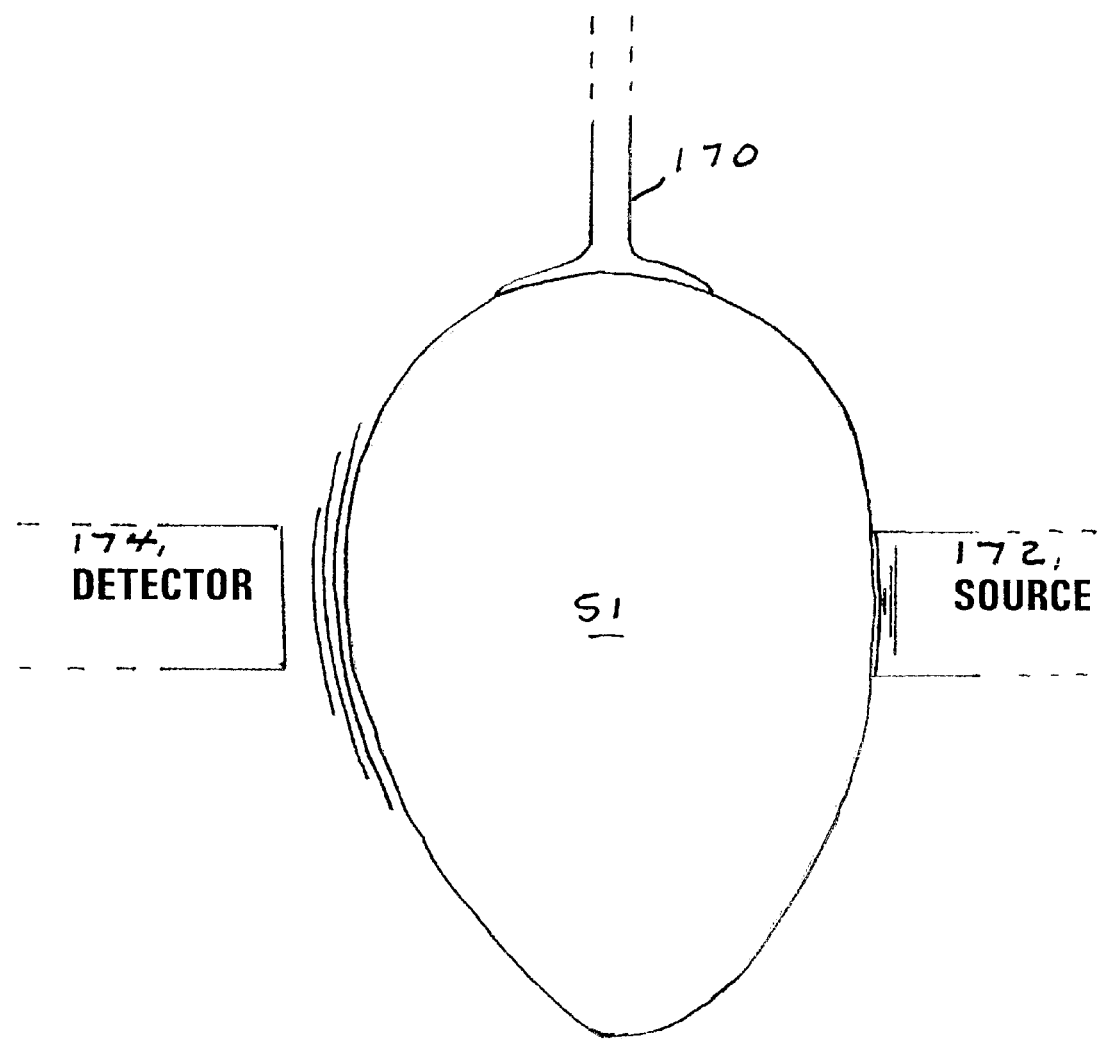

FIG. 17 is an elevational view of a vertically-oriented egg 51 having its pointed end downward. A down-stroke contacting device 170 contacts the egg 51's large end by a suction cup to lift the egg 51 and dispose it such that the egg 51's equator is disposed between a pair of opposed transducers 172 and 174, somewhat comparable to FIG. 1, except that the source transducer 172 contacts the egg 51's equator while the detector 174 is situated to operate in a non-contact mode. It is preferred in FIG. 17 that the process is accomplished in a sequence of cycles wherein originally the contacting device 170 positions the egg 51 in an examination position, and then the contact source 172 cycles to contact the egg 51 then withdraw. Following that, the contacting device 170 is free to dispose the egg 51 elsewhere.

Figure 18:
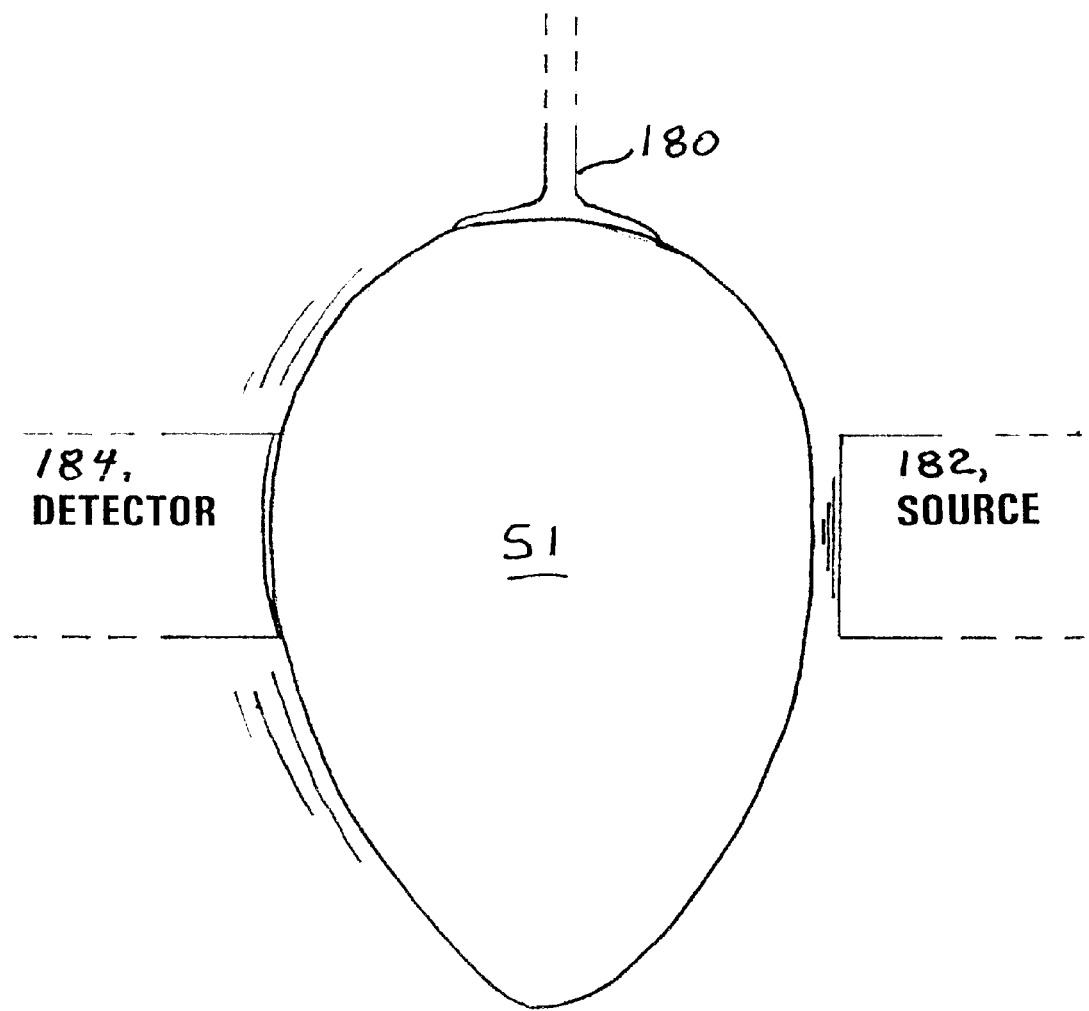

FIG. 18 is an elevational view comparable to FIG. 18, likewise showing a vertically-oriented egg 51 with pointed end downward. A down-stroke contacting device 180 contacts the egg 51's large end by a suction cup to lift the egg 51 and dispose it such that the egg 51's equator is disposed between a pair of opposed transducers 182 and 184, wherein by this arrangement the source transducer 182 is spaced away from the egg 51's equator to operate in non-contact mode while the detector 184 is situated in contact with the egg 51's equator. As described in connection with FIG. 17, preferably the contacting device 180 moves the egg 51 into an examination position and then the contacting detector 184 cycles into contact with the egg 51's equator. Following examination, the contacting 184 retracts and then the contacting device 180 is free to dispose the egg 51 elsewhere.

Figure 19:
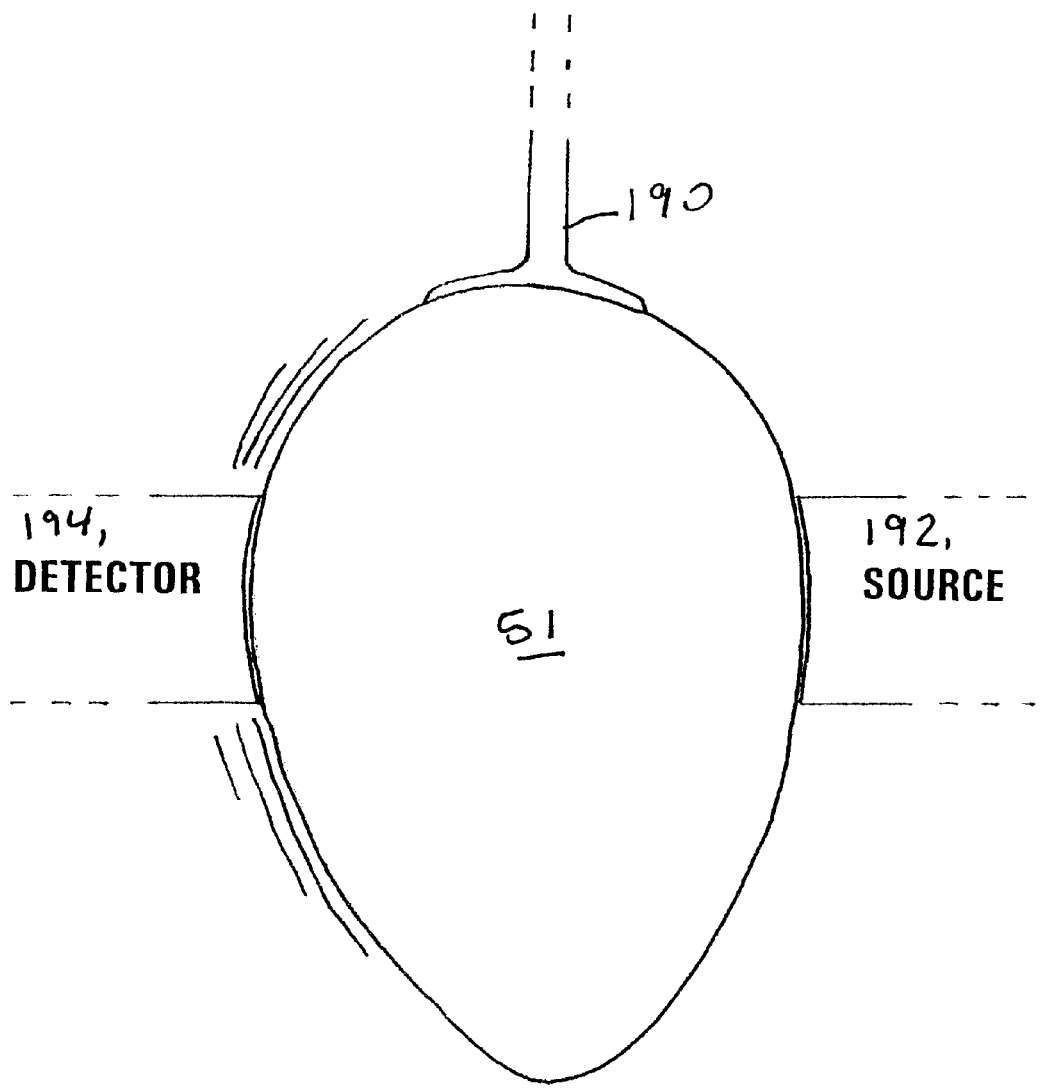

FIG. 19 continues the theme of the previous two views, again showing a vertically-oriented egg 51 with pointed end downward. A down-stroke contacting device 190 contacts the egg 51's large end by a suction cup to lift the egg 51 and dispose it such that the egg 51's equator is disposed between a pair of opposed transducers 192 and 194, wherein by this arrangement both the source transducer 192 and the detector 194 are cycled in strokes to contact the egg's equator on opposite sides thereof. The sequence of operations would preferably have the contacting device 190 disposing the egg 51 into an examination position, after which the source and detector would be driven into contact with the egg 51 on opposite positions on its equator. Following examination, the probes 192 and 194 would retract and then the contacting device 190 is free to dispose of the egg 51 elsewhere.

Figure 20:
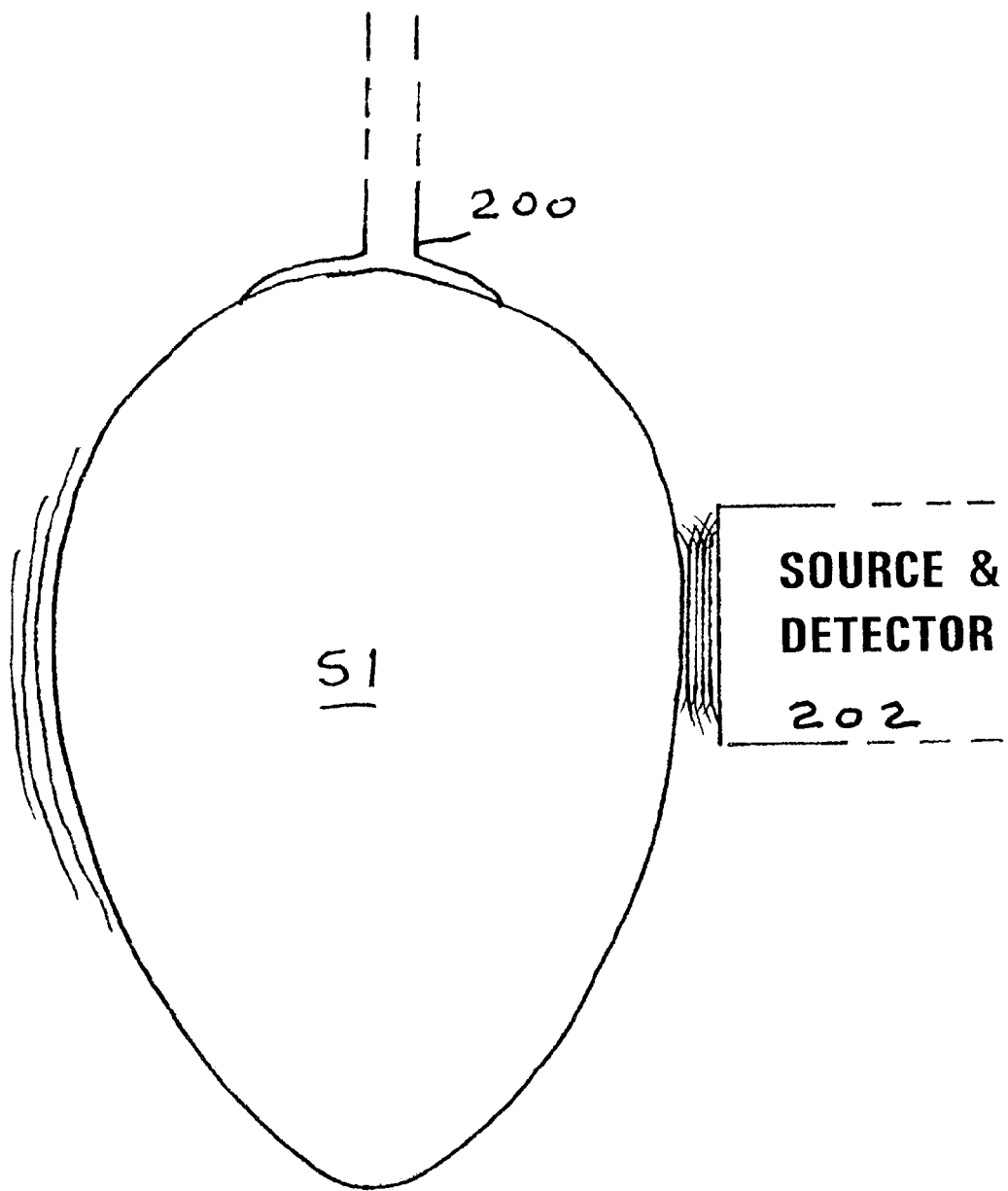

FIG. 20 is an elevational view showing a vertically-oriented egg 51 with pointed end downward being oriented by a down-stroke contacting device 200 contacting the egg 51's large end to move the egg 51 into an examination position such that a non-contact probe 202 aimed at a target on the egg 51's equator combines both source and detector functions.

In general, the advantages of non-contact probes include among other advantages, the advantage that non-contact probes in contrast to contact probes can be relied on to operate suitably from stationary mountings. That is, with non-contact probes, external devices such as the illustrated suction-cup type contacting devices are relied on to move the egg into an examination position. A non-contact probe merely sits stationary awaiting eggs to be brought to it. In contrast, contact probes will generally incorporate a cyclical movement comprising a contacting stroke for one-half of the cycle, followed by a retraction stroke on the other half of the cycle. While the contact probe idles in the retracted position, various external positioning devices are relied on to move the egg into an examination position in which the contacting probe can then cycle through its movement and hit its target.

Figure 21:
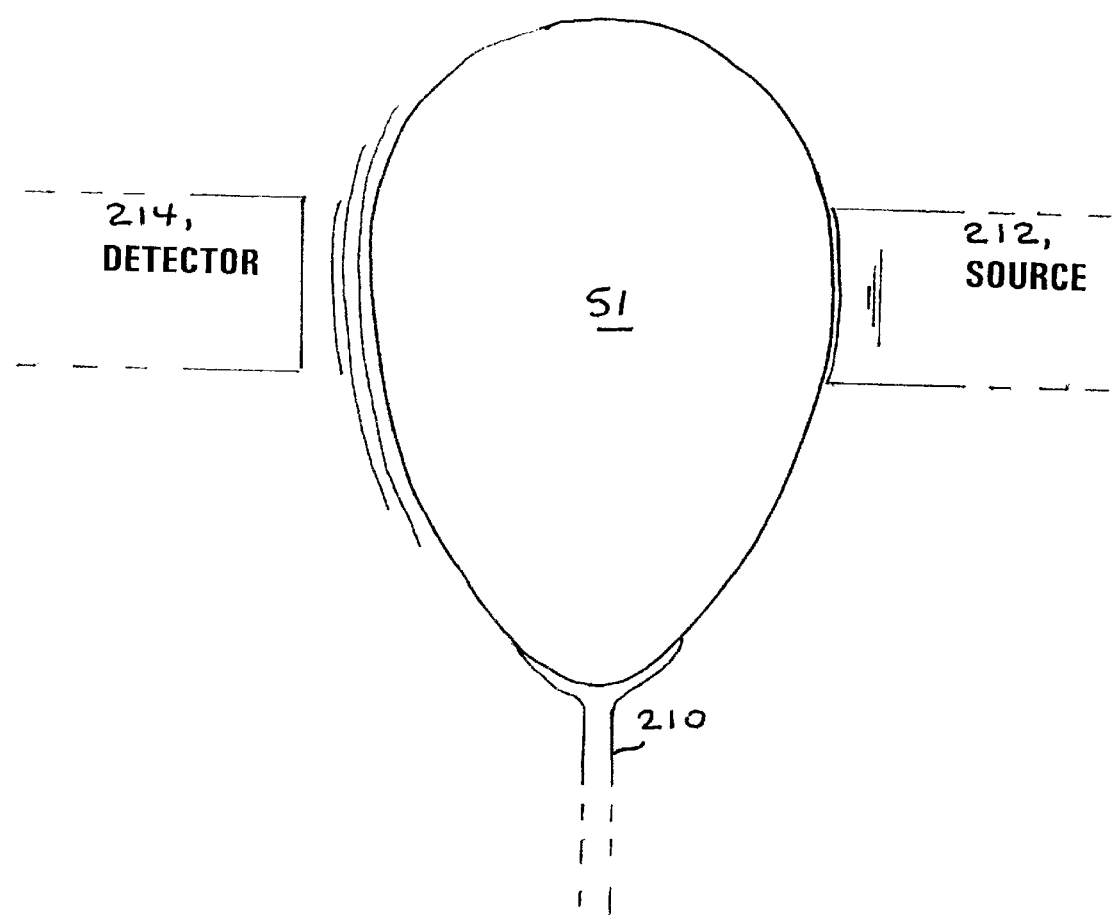

FIG. 21 is an elevational view comparable to FIG. 17 except that an up-stroke contacting device 210 meets a vertically-oriented egg 51's pointed end to move it into an examination position between a contacting source probe 212 and non-contact detector 214 on opposite sides of the egg 51's equator. The sequence of operations preferably has the contacting device 210 positioning the egg 51 in the examination position, followed by the contact source 212 cycling to contact the egg 51 then withdraw. Following that, the contacting device 210 is free to dispose the egg 51 elsewhere.

Figure 22:
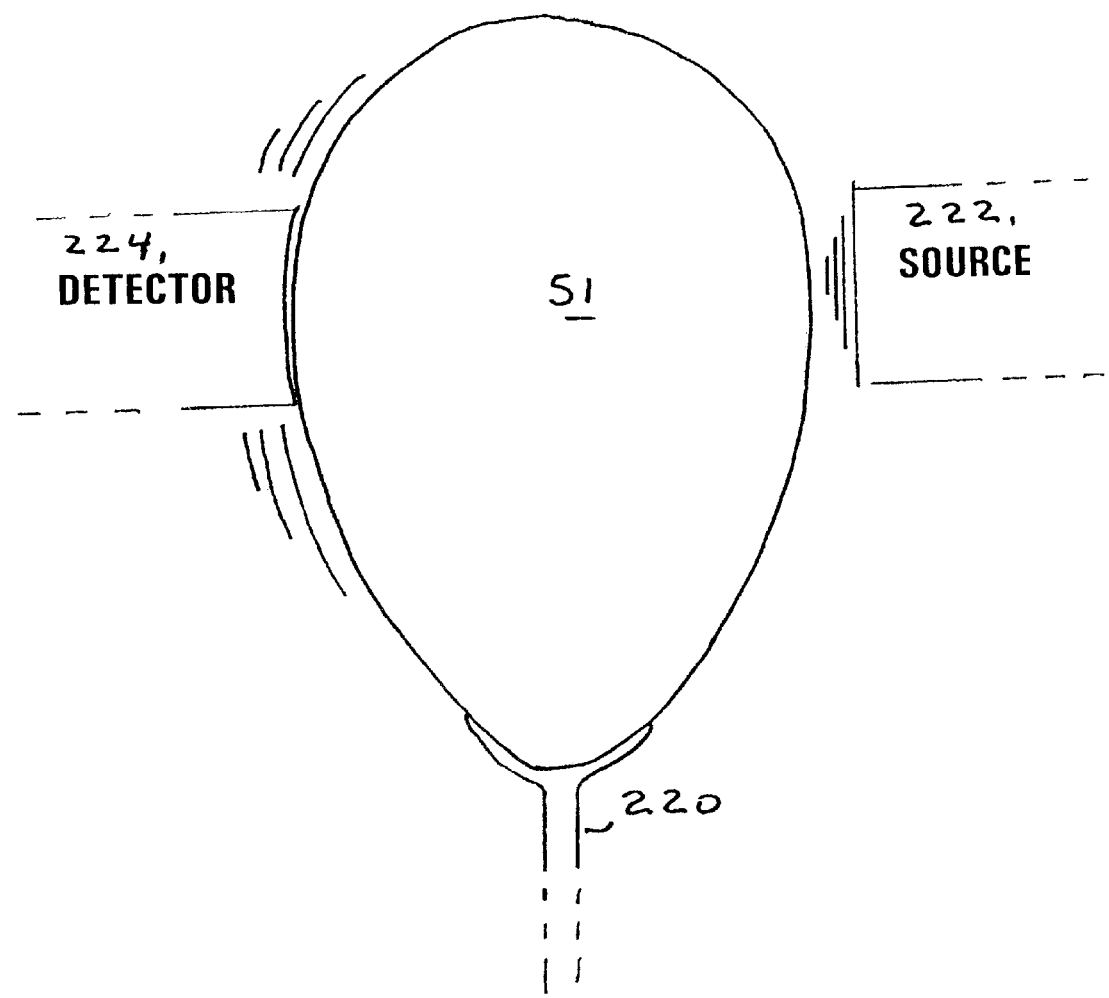

In a comparable way as between FIGS. 21 and 17, FIG. 22 corresponds to FIG. 18, wherein an up-stroke contacting device 220 meets a vertically-oriented egg 51's pointed end to move it into an examination position between a non-contact source probe 222 and a contact detector 224 on opposite sides of the egg 51's equator. The sequence of operations preferably has the contacting device 220 positioning the egg 51 in the examination position, followed by the contact detector 224 cycling to contact the egg 51 then withdraw. Following that, the contacting device 220 is free to dispose the egg 51 elsewhere.

Figure 23:
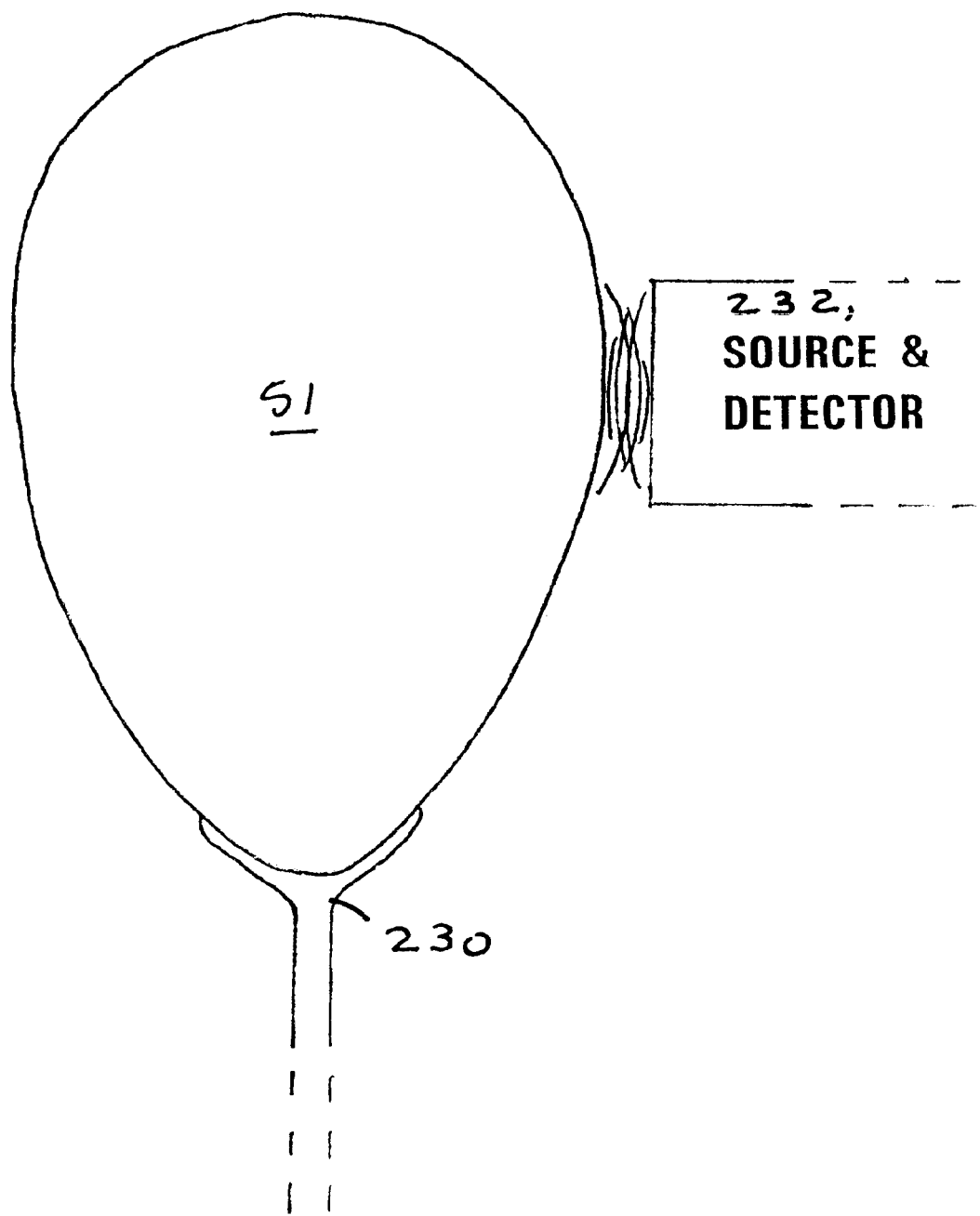

Moreover, FIG. 23 corresponds in the same way to a previous view, FIG. 20, in that a vertically-oriented egg 51 with pointed end downward is oriented by an up-stroke contacting device 230 contacting the egg 51's downward-oriented pointed end to move the egg 51 into an examination position aside a non-contact probe 232 aimed at a target on the egg 51's equator. The non-contact probe 232 combines both source and detector functions.

Figure 24:
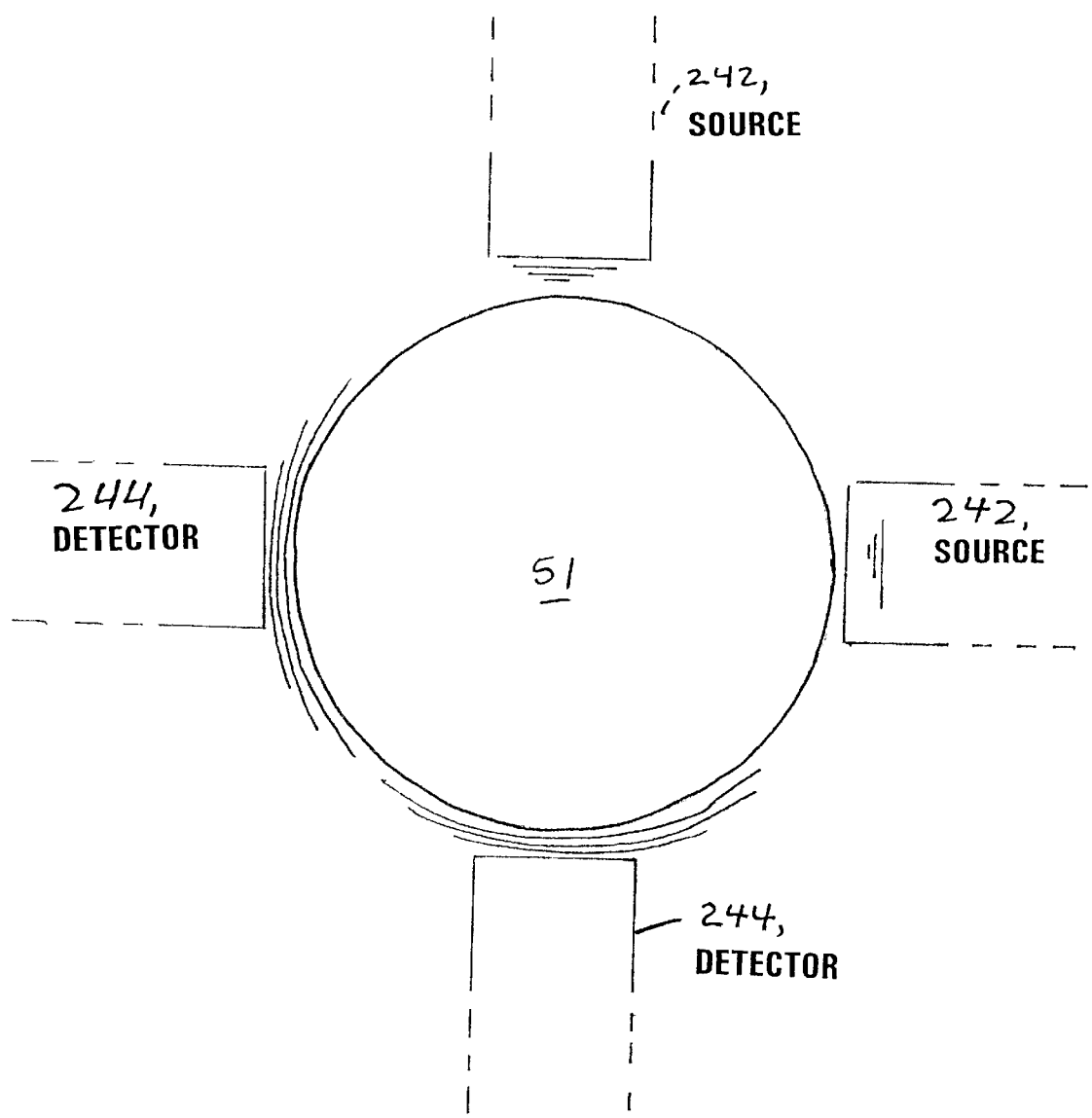
FIGS. 24 and 25 are top plan views.
Figure 25:
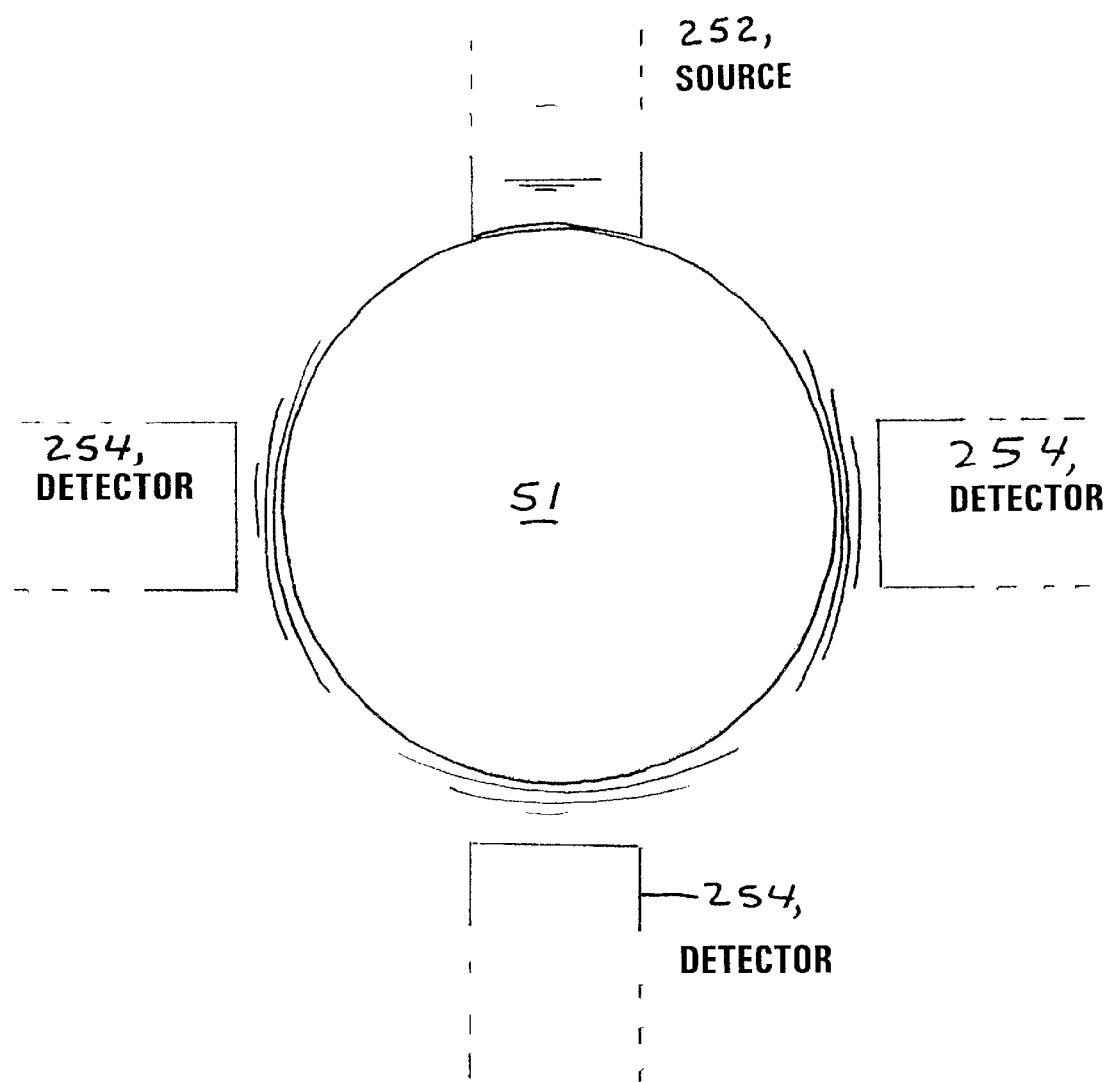

FIGS. 24 and 25 depart somewhat from the previous views including FIG. 1 and then the series of 8 through 23. FIGS. 24 and 25 can be reckoned as top plan views of a vertically-oriented egg 51, it not really mattering whether the pointed end it up or down. Presumptively a contacting device (not shown) from either above or below is aimed to contact the upper or lower end of the vertically-oriented egg 51 to move such egg 51 into the examination position as show in FIGS. 24 or 25. These FIGS. 24 and 25 show an assortment of probes, generally four in each view, arranged in a common horizontal plane and targeted at equidistant spacings around the aquator of the egg 51.

In other words, FIG. 24 shows non-contact source probes 242 at the twelve and thee o'clock positions (eg., the reference twelve o'clock position being arbitrary given an egg's presumed symmetry around its equator). Correspondingly, a corresponding pair of non-contact detector 244 are arranged in opposition to respective ones of the sources probes 242, which pair of detector probes sit at the six and nine o'clock positions. Multiple advantages are provided by this arrangement. Finer signal analysis can be obtained. If both source probes 242 are operating on the same frequency and same power, differential analysis of the dectected signal obtained the detector probes 244 will show matters not readily obtained by a single pair of source and detector probes. Additionally, the source probes 242 can be operated under different conditions such as differing frequencies, such that different frequencies may reveal the presence or absence of differing factors relating to egg quality, Perhaps a single source probe could be stepped though an operative sequence to transmit at differing frequencies at different time frames, or transmit at two or more discrete bandwidths at the same time. However, the arrangement of FIG. 24 allows different source probes 242 to operate on different frequencies at the same time, whereby the mixed oscillations induced by the different sources 242 is detectable by one or more detectors 244 for analysis of richer information tha otherwise obtainable. In this arrangement it is preferred if all the probes 242 and 244 operate in non-contact mode.

FIG. 25 is top plan view comparable to FIG. 24 except showing an arrangement of four probes in which only a single probe 252 is a source probe as the other three evenly-spaced probes 254 are detector probes. The single source probe 252 is shown operating in contact mode albeit this is shown in the view for convenience only as the source probe 252 can be readily configured to operate in a non-contact mode. Likewise the detector probes are shown in non-contact operative positions albeit this too can be readily re-configured such that detector probes 254 operate in contact mode. Regardless, the array of plural detector probes 254 permit differential analysis in ways in which is not obtainable with a single detector.

Given the foregoing, the operative principles of the inventive apparatus and method include the following. Briefly, ultrasonic energy is used to "ping" an egg 51 and induce the 5 shell to chime a like a tuning fork. The emanated energy is "listened" to. If the detected energy "sounds" in ways which trials and experience correlate to quality shells, the shell is reckoned as being of good quality. If not or, that is, if the egg clangs off-note like an old metal platter dropped on the floor, the shell is reckoned as being of poor quality. Information on shell quality obtained this way is correlated to predictive models for egg quality. A use decision is made based upon the predicted egg quality and the egg is sorted accordingly.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. A method for determining whether avian eggs are qualified or unqualified for a premium quality based on shell characteristics, comprising the steps of:

providing a plurality of the eggs;

oscillating the shells of each egg by a non-contacting ultrasonic-wave source that needs only a single nominal operating frequency in order to propagate a spectrum of effects in the oscillating shells that is detectable by a non-contacting detector, wherein said spectrum can be graphed according to the different time-of-flight at which a select effect propagated from the source to the detector; and determining whether each egg is qualified or not from spectrum analysis;

wherein the select effect comprises detected signal power as a variable against that signal's detected time-of-flight from source to detector such that said spectrum can be graphed against a vertical axis for detected-power versus a horizontal axis for the corresponding time-of-flight, wherein said spectrum as graphed so is analyzed for a positive indication consisting of at least two sufficiently strong peaks of detected-power along the time-of-flight axis within a chosen bandwidth of time-of-flight, and further that the two peaks are sufficiently steady over a sufficient amount of analysis time, wherein the positive indication is correlatable to a given quality determination of egg shell quality.

2. The method of claim 1 wherein the analysis comprises integrated response (IR) analysis of the spectrum or at least the chosen bandwidth.

3. The method of claim 1 wherein the given quality determination of egg turn is associated with such a quality determination of the avian egg as relating to fertility or hatching or hatchling viability.

4. The method of claim 1 wherein the power spectrum excludes power information for times of time-of-flight longer than that corresponding to a reference time-of-flight value obtained in the absence of any egg or other object between the source and detector, which longer times of time-of-flight correspond to noise.

5. The method of claim 1 wherein eggs qualified for premium quality are graduated to hatchery operations.

6. A method for sorting out sub-grade avian eggs from premium grade avian eggs comprising the steps of:

providing a plurality of the eggs;

positioning each egg in the path of a non-contacting, non-frequency sweeping source of ultrasonic waves and in relative proximity to a non-contacting detector of a signal obtained from the egg under the influence of the ultrasonic waves;

wherein said signal contains a spectrum of influences in the shells that are product of the source ultrasonic waves such that said spectrum can be graphed according to the different time at which a select influence propagated from the source to the detector; and determining the eggs as premium grade or sub-grade based upon spectrum analysis;

wherein the select influence which is sought after for detection and analysis comprises detected-signal strength such that said spectrum is transformable into a profile of detected signal strength versus time from source to detector, wherein said spectrum is analyzed for a positive indication of premium grade comprising at least two sufficiently strong peaks of detected-signal strength in the profile thereof, which said at least two peaks are furthermore analyzed for ability in contrast to inability to remain sufficiently steady all while during the analysis thereof.

7. The method of claim 6 wherein the analysis comprises integrated response (IR) analysis of the detected signal's strength versus time profile.

8. The method of claim 6 wherein the positive indication of premium grade is correlatable to egg shell quality which in turn is associated with such a quality determination of the avian egg as relating to fertility or hatching or hatchling viability.

9. The method of claim 6 wherein the spectrum excludes signal strength information for times longer than that corresponding to a reference time value obtained in the absence of any egg or other object between the source and detector.

10. The method of claim 6 wherein eggs determined to be premium grade are graduated to hatchery operations.

11. Apparatus for determining premium grade avian eggs from sub-grade avian eggs comprising:

a source of ultrasonic waves from which is required only a single nominal operating frequency and an opposed ultrasonic detector in the path thereof spaced sufficiently to admit therebetween an egg without contact from either, wherein one sample analysis of the egg obtains a sustained spectrum of signals detectable by the detector in response to blocking the path of a sustained transmission of the ultrasonic waves from the source;

wherein said spectrum of said one sample can be plotted according to the different time-of-flight at which a select signal propagated from the source to the detector; and a processor for determining the eggs as premium grade or not based upon spectrum analysis;

wherein the processor includes services of an analyzer that plots the spectrum of said one sample into a profile comprising, as along one axis, detected strengths of the various select signals versus, as along another axis, time-of-flight from source to detector for each, wherein said spectrum is analyzed for a positive indication of premium grade comprising at least one sufficiently strong peak of detected-signal strength in a chosen bandwidth of times-of-flight, which at least one peak is furthermore analyzed for ability in contrast to inability to remain sufficiently steady over several succeeding sample analyses thereof.

12. The apparatus of claim 11 wherein the analyzer undertakes integrated response (IR) analysis over the chosen bandwidth.

13. The apparatus of claim 11 wherein the positive indication of premium grade is correlatable to egg shell quality which in turn is associated with such a quality determination of the avian egg as relating to fertility or hatching or hatchling viability.

14. The apparatus of claim 11 wherein the spectrum excludes signal strength information for times of time-of-flight longer than that corresponding to a reference time-of-flight value obtained in the absence of any egg or other object between the source and detector, which reference time-of-flight of values is obtained previously during set-up before sampling analysis of eggs is undertaken.

15. The apparatus of claim 11 wherein eggs determined to be of premium grade are graduated to hatchery operations.

* * * * *